(12) United States Patent
Dickson et al.

(10) Patent No.: US 11,725,032 B2
(45) Date of Patent: Aug. 15, 2023

(54) TREATMENT OF MUSCULAR DYSTROPHIES

(71) Applicant: Royal Holloway And Bedford New College, Egham (GB)

(72) Inventors: George Dickson, Egham (GB); Linda Popplewell, Egham (GB)

(73) Assignee: Royal Holloway And Bedford New College, Surrey (GB)

( * ) Notice: Subject to any disclaimer, the term of this patent is extended or adjusted under 35 U.S.C. 154(b) by 409 days.

(21) Appl. No.: 16/770,358

(22) PCT Filed: Dec. 5, 2018

(86) PCT No.: PCT/GB2018/053521
§ 371 (c)(1),
(2) Date: Jun. 5, 2020

(87) PCT Pub. No.: WO2019/110988
PCT Pub. Date: Jun. 13, 2019

(65) Prior Publication Data
US 2021/0130426 A1  May 6, 2021

(30) Foreign Application Priority Data
Dec. 5, 2017 (GB) ..................... 1720224

(51) Int. Cl.
C07K 14/47 (2006.01)
C12N 15/86 (2006.01)

(52) U.S. Cl.
CPC .......... C07K 14/4707 (2013.01); C12N 15/86 (2013.01); *C12N 2750/14141* (2013.01)

(58) Field of Classification Search
CPC .............. A61K 48/005; A61K 48/0058; C07K 14/4707; C07K 14/4708; C12N 15/102;
(Continued)

(56) References Cited

U.S. PATENT DOCUMENTS

| 11,078,247 B2 * | 8/2021 | Fotin-Mleczek .... C07K 14/505 |
| 2019/0241633 A1 * | 8/2019 | Fotin-Mleczek .. A61K 31/7088 |
| 2022/0025369 A1 * | 1/2022 | Fotin-Mleczek .. A61K 31/7088 |

FOREIGN PATENT DOCUMENTS

| EP | 2960336 A1 | 12/2015 |
| WO | 2016/177911 A1 | 11/2016 |
| WO | 2017/191274 A2 | 11/2017 |

OTHER PUBLICATIONS

GenBank: LF450158.1, JP 2015516143-A/44529: Modified Polynucleotides for the Production of Proteins Associated With Human Disease (Oct. 28, 2016), available at https://www.ncbi.nlm.nih.gov/nuccore/LF450158.1/ (last visited Aug. 15, 2022) (Year: 2016).*

(Continued)

*Primary Examiner* — Randall L Beane
(74) *Attorney, Agent, or Firm* — Banner & Witcoff, Ltd.

(57) ABSTRACT

There is described a nucleic acid molecule comprising a nucleotide sequence encoding a functional dystrophin protein. Also described is a vector, a host cell and a pharmaceutical composition comprising the nucleic acid molecule; use of the nucleic acid molecule in therapy, such as in the treatment of a muscular dystrophy; and a method of treating muscular dystrophy, the method comprising administering a therapeutically effective amount of the nucleic acid molecule to a patient suffering from a muscular dystrophy.

19 Claims, 7 Drawing Sheets

Specification includes a Sequence Listing.

(58) Field of Classification Search
CPC .......... C12N 15/86; C12N 2740/16043; C12N 2750/14141; C12N 2750/14143
See application file for complete search history.

(56) References Cited

OTHER PUBLICATIONS

Aug. 30, 2018—(UK) Search Report—App No. GB1720224.3.
Human Gene Therapy, vol. 25, Feb. 2014, Koo et al., "Triple Trans-Splicing Adeno-Associated Virus Vectors Capable of Tranferring the Coding Sequence for Full-Length Dystrophin Protein into Dystrophic Mice", pp. 98-108.
Toby Maslin, Apr. 10, 2015, "Developing gene therapy for Duchenne muscular dystrophy", Muscular Dystrophy UK, [online], Available from: http://www.musculardystrophyuk.org.
Nucleic Acids Research, vol. 41, No. 17, Jul. 2013, Lorain et al., "Dystrophin rescue by trans-splicing: a strategy for DMD genotypes not eligible for exon skipping approaches", pp. 8391-8402.
Molecular Therapy, vol. 16, No. 11, Nov. 2008, Foster et al., "Codon and mRNA Sequence Optimization of Microdystrophin Transgenes Improves Expression and Physiological Outcome in Dystrophic mdx Mice Following AAV2/8 Gene Transfer", pp. 1825-1832.
Mar. 1, 2019—International Search Report—App No. PCT/ GB2018/053521.
Human Gene Therapy, vol. 23, Jul. 2012, Foster et al., "Genetic Therapeutic Approaches for Suchenne Muscular Dystrophy", pp. 676-687.
Jarmin et al., "New developments in the use of gene therapy to treat Duchenne muscular dystrophy" Expert Opinion on Biological Therapy; Feb. 2014; vol. 14; Issue 2; pp. 209-230.

\* cited by examiner

TREATMENT OF MUSCULAR DYSTROPHIES

FIELD OF THE INVENTION

The present invention relates to a codon optimised dystrophin coding sequence. The invention also relates to vectors comprising the codon optimised dystrophin coding sequence, the use of the codon optimised dystrophin coding sequence in treating muscular dystrophies and methods of treating muscular dystrophies involving the codon optimised dystrophin coding sequence. Muscular dystrophies that can be treated include Duchenne muscular dystrophy (DMD).

BACKGROUND TO THE INVENTION

Duchenne Muscular Dystrophy is an X-linked inherited condition with an incidence of 1 in 3000-5000 boys. The DMD gene encodes dystrophin, a molecular linker between the intracellular actin and extracellular matrix, crucial to correct muscle contractility and integrity. In the absence of this protein, eccentric contractions result in muscle damage as contractile force may not be dissipated correctly, in the short-term muscle can be regenerated by satellite cells. Continued cycles of contraction and regeneration, propagates muscle fibrosis, scarring and ultimately lipid invasion. Initially this manifests within the proximal skeletal muscles of the limbs, reducing the child's mobility, before eventually progressing to respiratory and cardiac systems, requiring invasive support systems and ultimately causing death between the second and third decade of life.

Currently, the vast majority of gene and therapy approaches are focused upon the restoration of a shortened yet semi-functional dystrophin, producing a clinically lessoned, Becker muscular dystrophy phenotype by addressing specific patient mutations. Some of the current approaches include:

- Truncated microdystrophin AAV vectors are in development for DMD gene therapy, but clearly key domains of the full-length protein have been removed and the microdystrophin may be sub-optimal in skeletal muscle, smooth muscle, heart, and CNS locations.
- Antisense oligonucleotide approaches aiming to mask an mRNA splice site and facilitate the skipping of an exon. The major target is exon 51. However, due to the significant number of exons in which a mutation can occur, the therapeutic applicability of each antisense oligonucleotide is relatively low.
- Multiplex CRISPR-mediated deletion across exons 45-55, thereby removing a major mutation hotspot. This is applicable to approximately 68% of patients.
- NHEJ-mediated genome editing approaches whereby the microinsertions and deletions (InDels) occurring as a byproduct of the NHEJ DNA repair pathway are utilized in 1 in 3 cases to restore the reading frame.

A major limitation of these approaches is only certain patient cohorts can benefit from such therapies.

In view of the limitations in the current approaches, it would be preferable to develop a treatment approach which is more universal in nature so that it could be applied to a larger proportion of patients. Further, it would be advantageous if the whole dystrophin protein could be restored rather than a truncated form of it.

SUMMARY OF THE INVENTION

The inventors have designed an optimised cDNA sequence encoding full-length human dystrophin. This provides improved protein expression compared to the native wild-type human gene sequence.

Therefore, in a first aspect, there is provided a nucleic acid molecule comprising a nucleotide sequence encoding a functional dystrophin protein, wherein the nucleotide sequence has at least 77% identity to the sequence of SEQ ID NO. 1.

The optimised cDNA sequence encoding full-length human dystrophin has been shown to produce about a 22-fold increase in protein expression compared to the native sequence.

In a second aspect, there is provided a vector for expressing a dystrophin protein, the vector comprising the nucleic acid molecule described above. This means that the vector contains a nucleotide sequence encoding a functional dystrophin protein so that when this sequence is expressed, a functional dystrophin protein is produced by the cell in which the vector is contained.

In a further aspect, there is provided a pharmaceutical composition comprising a nucleic acid molecule or a vector as described above and one or more pharmaceutically acceptable excipients.

In additional aspects, there is provided the use of a nucleic acid molecule or a vector described above in therapy, for example, in the treatment of muscular dystrophies, and a method of treating muscular dystrophies comprising administering a therapeutically effective amount of a nucleic acid molecule or a vector as described above to a patient suffering from a muscular dystrophy.

DETAILED DESCRIPTION OF THE INVENTION

As indicated above, there is provided a nucleic acid molecule comprising a nucleotide sequence encoding a functional dystrophin protein, wherein the nucleotide sequence has at least 77% identity to the sequence of SEQ ID NO. 1.

The sequence of SEQ ID NO. 1 is a codon optimised nucleotide sequence encoding the full-length human dystrophin protein. The dystrophin nucleotide sequence was optimised by taking into account the following desired parameters: to avoid where applicable cis-acting motifs including internal TATA boxes, chi-sites and ribosomal entry, AT or GC rich sequence stretches, RNA instability motifs, repeat sequences and RNA secondary structures, and cryptic splice donor and acceptor sites in higher eukaryotes. The cDNA sequence alterations have the effect of increasing translational efficiency, mRNA stability, gene transcription and consequently protein synthesis, thus enhancing the level of transgene product per unit of gene transferred. As a result, this nucleotide coding sequence has surprisingly been found to produce about a 22-fold increase in protein expression compared to the native gene sequence. This increase was not expected by the inventors when producing the sequence.

Codon optimisation of sequences has been known for some time. However, the results of this have been mixed. Codon optimising any particular sequence does not necessarily result in an increase in protein expression. Often, expression is the same and sometimes worse compared to the native sequence. Further, where there is an increase in expression, the degree of improvement can also vary significantly, with an increase of less than 10-fold being quite common. As a result, when codon optimising a sequence, there is no expectation that this will result in an increase in protein expression, and there is certainly no expectation that this will result in an increase in expression of more than 5-10 fold. Certainly, you would not expect to achieve an increase of about 22-fold as for the sequence disclosed herein.

Further, there are a number of algorithms which are used in the codon optimisation of sequences and these different algorithms produce different sequences as a result of the optimisation process. These different sequences generally produce different levels of protein expression. However, no one algorithm consistently produces better results than the others. As a result, it is not possible to predict which codon optimisation algorithm will provide the best results for any particular sequence.

With regard to dystrophin, whilst groups have previously tried codon optimising microdystrophin constructs, the results of codon optimisation of full-length dystrophin has not been reported. Therefore, the approach used by the inventors is unconventional compared to other research in this area. Further, in view of the fact that no results have been reported on the codon optimisation of full-length dystrophin, there was no expectation that this approach would be successful, let alone produce the surprising results that have been demonstrated by the inventors.

The DMD gene, encoding the dystrophin protein, is one of the longest human genes known, covering 2.3 megabases (0.08% of the human genome). The primary transcript in muscle measures about 2,100 kilobases and takes 16 hours to transcribe. The mature mRNA measures 14.0 kilobases. The 79-exon muscle transcript codes for a protein of 3686 amino acid residues. Mutations in the DMD gene cause a number of muscular conditions, including Duchenne muscular dystrophy (DMD), Becker muscular dystrophy (BMD) and cardiomyopathy.

Previous attempts to address the mutations in the dystrophin protein have focused on producing shorter, partially functional dystrophin variants which can reduce the severity of the muscular dystrophy. Despite many efforts, delivery of the full-length dystrophin gene has not occurred with any convincing expression levels. Mainly this has been the result of the large transgene, limited delivery processes and the native sequence being sub-optimal for expression. However, it is thought that the optimised dystrophin construct with increased expression may produce high enough levels of dystrophin to ameliorate the clinical phenotypes from a relatively low level of correction. As a result, existing strategies to repair the dystrophin gene/deliver the transgene could be employed enabling a more 'universal' therapeutic strategy, thereby overcoming the current mutation specific constraints in many therapeutic strategies.

The nucleotide sequence has at least 77% sequence identity to the sequence of SEQ ID NO. 1. In some embodiments, the nucleotide sequence has at least 78% identity to the sequence of SEQ ID NO. 1. In various embodiments, the nucleotide sequence has at least 79% identity to the sequence of SEQ ID NO. 1. In further embodiments, the nucleotide sequence has at least 80% identity to the sequence of SEQ ID NO. 1. In some embodiments, the nucleotide sequence has at least 81% identity to the sequence of SEQ ID NO. 1. In other embodiments, the nucleotide sequence has at least 82% identity to the sequence of SEQ ID NO. 1. In particular embodiments, the nucleotide sequence has at least 83% identity to the sequence of SEQ ID NO. 1. In further embodiments, the nucleotide sequence has at least 84% identity to the sequence of SEQ ID NO. 1. In some embodiments, the nucleotide sequence has at least 85% identity to the sequence of SEQ ID NO. 1. In other embodiments, the nucleotide sequence has at least 86% identity to the sequence of SEQ ID NO. 1. In particular embodiments, the nucleotide sequence has at least 87% identity to the sequence of SEQ ID NO. 1. In further embodiments, the nucleotide sequence has at least 88% identity to the sequence of SEQ ID NO. 1. In some embodiments, the nucleotide sequence has at least 89% identity to the sequence of SEQ ID NO. 1. In further embodiments, the nucleotide sequence has at least 90% identity to the sequence of SEQ ID NO. 1. In some embodiments, the nucleotide sequence has at least 91% identity to the sequence of SEQ ID NO. 1. In other embodiments, the nucleotide sequence has at least 92% identity to the sequence of SEQ ID NO. 1. In particular embodiments, the nucleotide sequence has at least 93% identity to the sequence of SEQ ID NO. 1. In further embodiments, the nucleotide sequence has at least 94% identity to the sequence of SEQ ID NO. 1. In some embodiments, the nucleotide sequence has at least 95% identity to the sequence of SEQ ID NO. 1. In other embodiments, the nucleotide sequence has at least 96% identity to the sequence of SEQ ID NO. 1. In particular embodiments, the nucleotide sequence has at least 97% identity to the sequence of SEQ ID NO. 1. In further embodiments, the nucleotide sequence has at least 98% identity to the sequence of SEQ ID NO. 1. In some embodiments, the nucleotide sequence has at least 99% identity to the sequence of SEQ ID NO. 1. In other embodiments, the nucleotide sequence has at least 99.5% identity to the sequence of SEQ ID NO. 1. In particular embodiment, the nucleotide sequence has the sequence of SEQ ID NO. 1. In certain embodiments, the nucleotide sequence has the sequence of SEQ ID NO. 3.

The nucleotide sequence encodes a functional dystrophin protein. A functional dystrophin protein is one which can form part of a protein complex known as the costamere or the dystrophin-associated protein complex, which acts as a transmembrane platform that anchors the extracellular matrix (ECM) to the intracellular cytoskeleton. The dystrophin protein has four main functional domains: an actin-binding amino-terminal domain; a central rod domain; a cysteine-rich domain and a carboxyl-terminus. These bind to a number of structures/proteins to allow dystrophin to correctly carry out its function in the dystrophin-associated protein complex. For example, dystrophin binds to actin filaments, microtubules and a number of proteins which help to anchor the dystrophin at the sarcolemma. A skilled person would readily be able to identify whether a dystrophin protein is functional. For example, this could be done by using an assay involving immunohistochemical staining of treated muscle sections, staining for dystrophin, and looking for restoration of the dystrophin-associated protein complex at the sarcolemma through staining (see Counsell J R et al., Sci Rep. 7:44775 (2017); Koo T et al., Hum Gene Ther. 25(2):98-108 (2014); Koo T et al., Hum Gene Ther. 22(11): 1379-88 (2011); Le Guiner C et al., Nat Commun. 8:16105 (2017); and Meng J et al., Sci Rep. 6:19750 (2016)).

In preferred embodiments, the nucleotide sequence encodes a functional human dystrophin protein. The sequences of appropriate dystrophin proteins are well known to those skilled in the art. For example, a number of dystrophin isoforms are known. Therefore, the nucleotide sequence may encode a dystrophin protein selected from isoform 1 (identifier: P11532-2), isoform 2 (identifier: P11532-3), isoform 3 (identifier: P11532-4) and isoform 4 (identifier: P11532-1). Preferably, the nucleotide sequence encodes isoform 4 (identifier: P11532-1) of the human dystrophin protein. The amino acid sequence of the native human dystrophin protein can be found as SEQ ID NO. 2.

Therefore, in some embodiments, the nucleotide sequence encodes a dystrophin protein having the amino acid sequence of SEQ ID NO. 2. Other dystrophin proteins that may be encoded by the nucleotide sequence include natural variants with mutations that do not affect the function of the dystrophin protein.

The human dystrophin protein is 3686 amino acids in length. Therefore, in some embodiments, the nucleotide sequence encodes a dystrophin protein having at least 3675 amino acids. In other embodiments, the nucleotide sequence encodes a dystrophin protein having at least 3680 amino acids. In further embodiments, the nucleotide sequence encodes a dystrophin protein having at least 3682 amino acids. In various embodiments, the nucleotide sequence encodes a dystrophin protein having at least 3683 amino acids. In certain embodiments, the nucleotide sequence encodes a dystrophin protein having at least 3684 amino acids. In particular embodiments, the nucleotide sequence encodes a dystrophin protein having at least 3685 amino acids.

In some embodiments, the nucleotide sequence encodes a dystrophin protein having at most 3697 amino acids. In other embodiments, the nucleotide sequence encodes a dystrophin protein having at most 3692 amino acids. In further embodiments, the nucleotide sequence encodes a dystrophin protein having at most 3690 amino acids. In various embodiments, the nucleotide sequence encodes a dystrophin protein having at most 3689 amino acids. In certain embodiments, the nucleotide sequence encodes a dystrophin protein having at most 3688 amino acids. In particular embodiments, the nucleotide sequence encodes a dystrophin protein having at most 3687 amino acids.

In particular embodiments, the nucleotide sequence encodes a dystrophin protein having about 3686 amino acids. In these embodiments, the nucleotide sequence can be said to encode a 'full-length' human dystrophin protein.

The nucleotide sequence encoding a dystrophin protein is preferably between 11,025 and 11,085 nucleotides in length. In some embodiments, the nucleotide sequence encoding a functional dystrophin protein is between 11,040 and 11,070 nucleotides in length. In other embodiments, the nucleotide sequence encoding a functional dystrophin protein is between 11,052 and 11,064 nucleotides in length. In particular embodiments, the nucleotide sequence encoding a functional dystrophin protein is about 11,058 nucleotides in length.

The nucleic acid molecule may comprise additional nucleotide sequences which encode further peptides/proteins or perform some further function, for example, aiding in the expression of the nucleotide sequence encoding the dystrophin protein. For example, the nucleic acid molecule may comprise a nucleotide sequence which encodes a green fluorescent protein (GFP) such that when the nucleic acid molecule is expressed, a dystrophin protein is produced which is tethered to the GFP.

Preferably, the nucleic acids described above are isolated.

It would be well with the capabilities of a skilled person to produce the nucleic acid molecules described above. This could be done, for example, using chemical synthesis of a given sequence with appropriate enzymatic ligation, where necessary.

The nucleic acid molecule can be any type of nucleic acid composed of nucleotides. The nucleic acid should be able to be expressed so that a protein is produced. Preferably, the nucleic acid is DNA or RNA. In some embodiments, the nucleic acid molecule is DNA, such as cDNA.

In a second aspect, there is provided a vector for expressing a dystrophin protein. The vector comprises the nucleic acid molecule described above. This means that the vector contains a nucleotide sequence encoding a functional dystrophin protein so that when this sequence is expressed, a functional dystrophin protein is produced by the cell in which the vector is contained.

In a therapeutic setting, the vector can take on a number of different forms depending on how the nucleic acid molecule is delivered to the cells of a patient suffering from a muscular dystrophy associated with a defective dystrophin protein. Various approaches are described in Chamberlain J R and Chamberlain J S ("Progress toward Gene Therapy for Duchenne Muscular Dystrophy", Mol Ther. 25(5):1125-1131 (2017)). For example, the nucleic acid molecule may be delivered by a transposon system (e.g. see Ley D et al., Stem Cell Res. 13(3 Pt A):390-403 (2014)), an artificial chromosome (e.g. see Tedesco F S, Chromosome Res. 23(1):135-41 (2015)), exploitation of the homology directed repair (HDR) DNA pathway (e.g. see Popplewell et al., Hum Gene Ther. (7):692-701 (2013)), a lentiviral vector (e.g. see Counsell J R et al., Sci Rep. 7(1):79 (2017)), or AAV vectors using a triple-transplicing approach (e.g. see Koo T et al., Hum Gene Ther. 25(2):98-108 (2014)).

In the triple-transplicing approach, the dystrophin cDNA is split across three adeno-associated viral vectors, which associate together in a directional manner when co-expressed due to corresponding splice acceptors and donors within each cassette. Alternatively, the sequence is split in three, each with a linked group 1 intron ribozymes, and each sequence expressed from an AAV vector leading to mRNAs which are spliced together in the correct order and orientation. Therefore, there is provided three AAV vectors, each containing a portion of the nucleic acid molecule described above, wherein following transduction of a cell with the three AAV vectors, the nucleic acid molecule is produced. In this context, the nucleic acid molecule may be produced as DNA or RNA (e.g. mRNA).

The exploitation of the homology directed repair (HDR) DNA pathway is a genetic engineering approach which involves production of a targeted DNA lesion in the DMD intron mediated by a specialised endonuclease and the exploitation of the HDR DNA pathway to integrate full-length dystrophin encoded by an exogenous cDNA donor.

In some approaches, stem cells may be isolated from a patient suffering from a muscular dystrophy associated with a defective dystrophin protein and these stem cells modified to incorporate the nucleic acid molecule described above, before the stem cells are reintroduced into the patient (e.g. see Zhu P et al., Mol Ther Nucleic Acids. 7:31-41 (2017) and Meng J et al., Sci Rep. 6:19750 (2016)). Alternatively, induced pluripotent stem cells may be used (e.g. see Gee Petal., Stem Cells Int. 2017:8765154 (2017)).

In certain embodiments in which the nucleic acid molecule is expressed by the vector (rather than being incorporated into the genetic material through a genetic engineering technique), the vector further comprises a promoter. The promoter causes expression of the nucleotide sequence encoding a functional dystrophin protein. Any appropriate promoter may be used, such as cytomegalovirus (CMV), Spc5.12, muscle creatine kinase (MCK), dMCK, tMCK, desmin (Des), alpha-myosin heavy chain ($\alpha$-MHC), myosin light chain 2 (MLC-2), cardiac troponin C (cTnC) and slow isoform of troponin I (TnIS). Preferably, the promoter is a muscle specific promoter such as Spc5.12, muscle creatine kinase (MCK), dMCK, tMCK, desmin (Des), alpha-myosin heavy chain (α-MHC), myosin light chain 2 (MLC-2), cardiac troponin C (cTnC) and slow isoform of troponin I (TnIS).

In vectors which are designed to integrate the dystrophin coding sequence into the genetic material of a cell rather than simply express the dystrophin coding sequence, for example by exploiting the homology directed repair (HDR) DNA pathway, the vector may not contain the entire dystrophin coding sequence (although in some embodiments, it may). Instead, it may contain a fragment of the dystrophin coding sequence which is then integrated into the defective sequence to bring about correction of the dystrophin sequence. Importantly, the fragment of the dystrophin coding sequence must be long enough so that it replaces the part of the defective dystrophin sequence containing the disease causing mutation. In this approach, the fragment of the dystrophin coding sequence may be integrated after the first few exons of the naturally occurring sequence or even later in the dystrophin sequence. For example, the vector may contain exons 2-79, or shorter variants such as 45-79 or even 53-79.

Therefore, in some embodiments, there is provided a nucleic acid molecule comprising at least exons 53 to 79 of a nucleotide sequence encoding a functional dystrophin protein, wherein the nucleotide sequence has at least 77% identity to the sequence of SEQ ID NO. 1. Further, there may be provided a nucleic acid molecule comprising at least exons 45 to 79 of a nucleotide sequence encoding a functional dystrophin protein, wherein the nucleotide sequence has at least 77% identity to the sequence of SEQ ID NO. 1. In addition, there may be provided a nucleic acid molecule comprising at least exons 10 to 79 of a nucleotide sequence encoding a functional dystrophin protein, wherein the nucleotide sequence has at least 77% identity to the sequence of SEQ ID NO. 1. In various embodiments, the nucleic acid molecule comprises at least exons 9 to 79 of the nucleotide sequence encoding a functional dystrophin protein. In other embodiments, the nucleic acid molecule comprises at least exons 8 to 79 of the nucleotide sequence encoding a functional dystrophin protein. In certain embodiments, the nucleic acid molecule comprises at least exons 7 to 79 of the nucleotide sequence encoding a functional dystrophin protein. In some embodiments, the nucleic acid molecule comprises at least exons 6 to 79 of the nucleotide sequence encoding a functional dystrophin protein. In various embodiments, the nucleic acid molecule comprises at least exons 5 to 79 of the nucleotide sequence encoding a functional dystrophin protein. In other embodiments, the nucleic acid molecule comprises at least exons 4 to 79 of the nucleotide sequence encoding a functional dystrophin protein. In certain embodiments, the nucleic acid molecule comprises at least exons 3 to 79 of the nucleotide sequence encoding a functional dystrophin protein. In some embodiments, the nucleic acid molecule comprises at least exons 2 to 79 of the nucleotide sequence encoding a functional dystrophin protein. The nucleotide sequence described in this paragraph may have at least 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identity to the sequence of SEQ ID NO. 1 as described with respect to the full sequence above. This means that the nucleic acid molecule comprises at least exons 10 to 79 of a nucleotide sequence encoding a functional dystrophin protein, wherein the nucleotide sequence has at least 78%, 79%, 80%, etc. identity to the sequence of SEQ ID NO. 1. This also applies to the rest of the statements above, e.g. the nucleic acid molecule may comprise at least exons 53 to 79, at least exons 45 to 79, at least exons 9 to 79, at least exons 8 to 79, at least exons 7 to 79, etc. of the nucleotide sequence encoding a functional dystrophin protein. Also provided is a vector comprising the nucleic acid molecule described above.

In some embodiments, the vector described above is a Puc57-human DMD intron 1 plasmid repair template as depicted in FIG. 6. In various embodiments, the vector described above is a lentiviral human DMD intron 1 plasmid repair template as depicted in FIG. 7.

The invention also provides a host cell comprising any one of the nucleic acid molecules or vectors described above. Preferably, the vector is capable of expressing the dystrophin nucleotide sequence in the host. The host may be any suitable host.

As used herein, the term "host" refers to cells which harbour a nucleic acid molecule or a vector, as well as cells that are suitable for use in expressing a recombinant gene or protein. It is not intended that the present invention be limited to any particular type of cell. Indeed, it is contemplated that any suitable cell will find use in the present invention as a host. A host cell may be in the form of a single cell or a population of similar or different cells, for example in the form of a culture (such as a liquid culture or a culture on a solid substrate). In some embodiments, the host cell may be a stem cell. This may be an autologous human stem cell or an induced pluripotent stem cell.

The host cell may permit the expression of the nucleic acid molecule. Thus, the host cell may be, for example, a bacterial, a yeast, an insect or a mammalian cell. Suitable mammalian cells may be from a human, a non-human primate, a rodent, especially a mouse, or may be canine, feline, ovine or porcine. Where the mammalian cell is a human cell, such as a stem cell, it is preferably isolated.

In one aspect, the invention provides a pharmaceutical composition comprising a nucleic acid molecule or a vector of the invention and one or more pharmaceutically acceptable excipients. The one or more excipients include carriers, diluents and/or other medicinal agents, pharmaceutical agents or adjuvants, etc.

The invention also provides a method of treating a muscular dystrophy, the method comprising administering a therapeutically effective amount of a nucleic acid molecule or a vector as described above to a patient suffering from the muscular dystrophy. Preferably, the patient is human.

The muscular dystrophy is associated with a mutation in the DMD gene. The muscular dystrophy may be selected from Duchenne muscular dystrophy (DMD), Becker muscular dystrophy (BMD) and cardiomyopathy.

When the muscular dystrophy is "treated" in the above method, this means that one or more symptoms of the muscular dystrophy are ameliorated. It does not mean that the symptoms of the muscular dystrophy are completely remedied so that they are no longer present in the patient, although in some methods, this may be the case. The method of treating results in one or more of the symptoms of the muscular dystrophy being less severe than before treatment.

A "therapeutically effective amount" refers to an amount effective, at dosages and for periods of time necessary, to achieve the desired therapeutic result, such as raising the level of (functional) dystrophin in a subject (so as to lead to dystrophin production at a level sufficient to ameliorate the symptoms of the muscular dystrophy).

Further, the invention provides the nucleic acid molecule encoding a functional dystrophin protein as described above, or a vector as described above for use in therapy, for example, in the treatment of a muscular dystrophy.

In addition, the invention provides the use of the nucleic acid molecule encoding a functional dystrophin protein as described above or a vector as described above in the manufacture of a medicament for treating a muscular dystrophy.

The invention also provides a method for delivery of a nucleotide sequence encoding a functional dystrophin protein to a subject, which method comprises administering to the said subject a nucleic acid molecule encoding a functional dystrophin protein as described above or a vector as described above.

In the description above, the term "identity" is used to refer to the similarity of two sequences. For the purpose of this invention, it is defined here that in order to determine the percent identity of two nucleotide sequences, the sequences are aligned for optimal comparison purposes (e.g., gaps can be introduced in the sequence of a first nucleic acid for optimal alignment with a second nucleic acid sequence). The nucleotide residues at nucleotide positions are then compared. When a position in the first sequence is occupied by the same nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length. A sequence comparison is typically carried out over the entire length of the two sequences being compared.

The skilled person will be aware of the fact that several different computer programs are available to determine the identity between two sequences. For instance, a comparison of sequences and determination of percent identity between two sequences can be accomplished using a mathematical algorithm. In a preferred embodiment, the percent identity between two nucleic acid sequences is determined using the sequence alignment software Emboss Stretcher (www.ebi.ac.uk/Tools/psa/emboss_stretcher) using the following pairwise alignment options: Matrix: DNAfull; Gap open: 16; Gap extend: 4; and Output format: Pair. An alternative option is to use Clone Manager 9 (Sci-Ed software—www.scied.com) using global DNA alignment; parameters: both strands; scoring matrix: linear (mismatch 2, OpenGap 4, ExtGap 1).

Alternatively, the percent identity between two nucleic acid sequences can be determined using the Needleman and Wunsch (1970) algorithm which has been incorporated into the GAP program in the Accelrys GCG software package (available at http://www.accelrys.com/products/gcg/), using either a Blosum 62 matrix or a PAM250 matrix, and a gap weight of 16, 14, 12, 10, 8, 6, or 4 and a length weight of 1, 2, 3, 4, 5, or 6. A further method to assess the percent identity between two nucleic acid sequences can be to use the BLAST sequence comparison tool available on the National Center for Biotechnology Information (NCBI) website (www.blast.ncbi.nlm.nih.gov), for example using BLASTn for nucleotide sequences using the default parameters.

All patent and literature references cited in the present specification are hereby incorporated by reference in their entirety.

BRIEF DESCRIPTION OF THE DRAWINGS

The invention will now be described in detail by way of example only with reference to the figures which are as follows.

Figure 6:
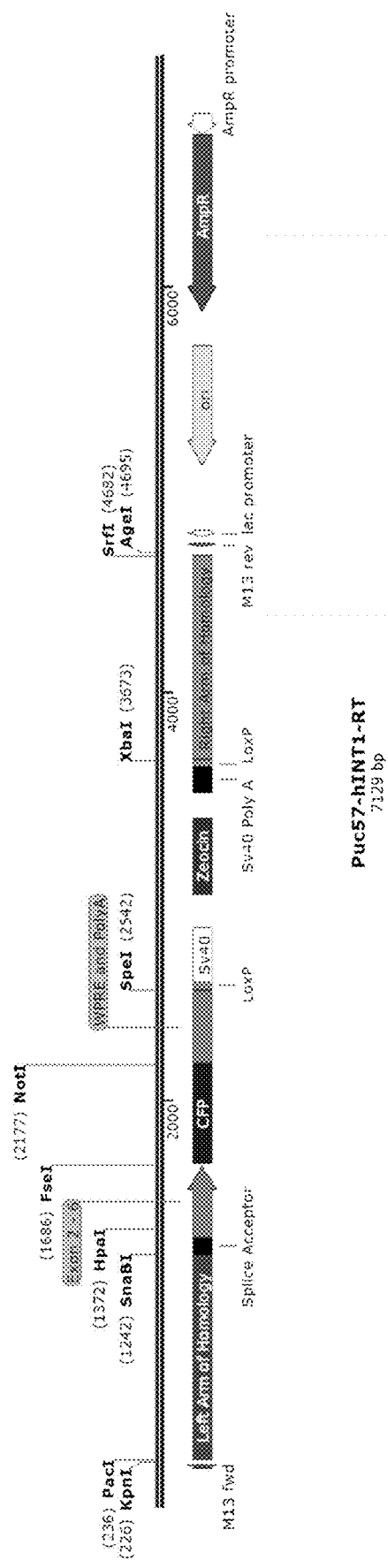

FIG. 6: A linear schematic of the Puc57-human DMD intron 1 plasmid repair template. A linear schematic of Puc57-hINT1-RT empty vector. The FseI and NotI sites flanking the Cyan fluorescent marker, serve as the directional cloning sites for the optimised full-length dystrophin. Upstream of this cloning site is a 1 kb left arm of homology, synthetic beta globin splice acceptor and Exons 2-6 of optimised DMD cDNA. Downstream of this cloning sequence is the WPRE and polyA to enhance expression. Followed thereafter by a floxed zeocin cassette, to facilitated selection and a 1 kb right arm of homology. Where possible these constituents are flanked by unique restriction sites that are annotated, ensuring that the repair template is amenable to changing constituents if required.

Figure 7:
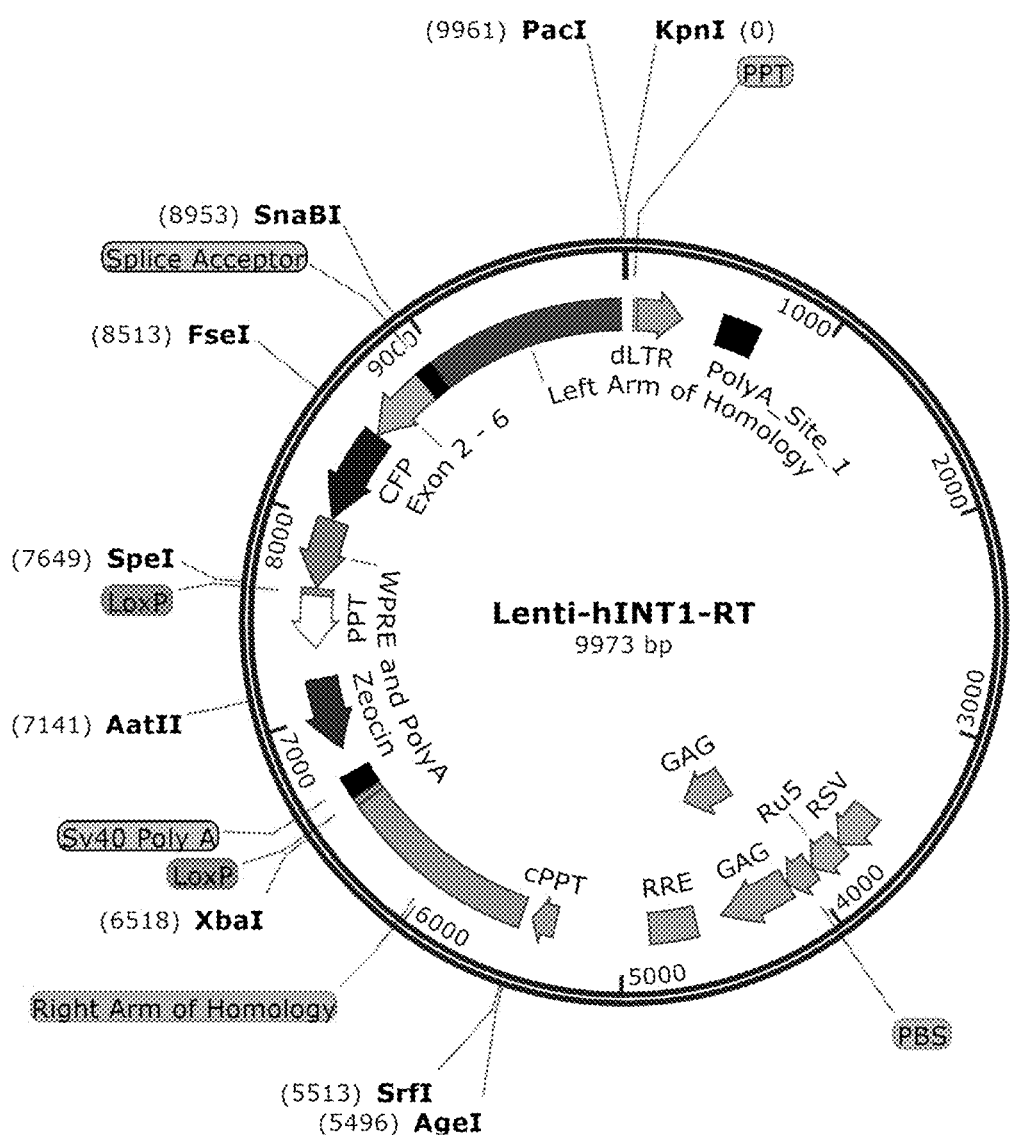

FIG. 7: A schematic of the Lentiviral human DMD intron 1 plasmid repair template. A lentiviral vector encoding the human DMD Intron 1 repair template; notably, the constituents of the human DMD intron 1 plasmid run in reverse orientation to the transcription of the lentiviral plasmid; this is to prevent aberrant splicing from occurring that may be detrimental to viral mRNA transcription and subsequently viral production. This includes the FseI and NotI cloning sites downstream of optimised DMD cDNA exons 2-6, CFP protein and Woodchuck hepatitis virus regulatory element (WPRE). In addition the upstream and downstream 1 kb arms of homology isogenic to the genomic sequence adjacent to the guide sites in intron 1 and the floxed zeocin cassette are also present.

EXAMPLES

This work was carried out to assess the expression of recombinant dystrophin protein resulting from both native and sequence optimised cDNA encoding full-length dystrophin.

Materials & Methods

Materials and Methods for characterisation of expression differences of full-length native and sequence optimised dystrophin:

Viafect Transient Transfection
Materials
Viafect Transient Transfection Reagent (Promega)
Serum Free Dulbecco's Modified Eagle's Medium (DMEM) (Gibco)
Hek293T Cells (ATCC)
Six Well Plate (Corning)
Sterile Eppendorfs (Corning)
Method Hek293T cells were seeded at a density of $5 \times 10^5$ at Day 0 to attain 70-80% confluency 24 hours post seeding. The growth media was carefully changed 1 hour prior to transient transfection. During this time, master mix was produced comprising: 20 µl of viafect reagent (Promega) and 4 µg of native or sequence optimised dystrophin made to a 200 µl volume per well using serum free DMEM (Gibco). Importantly, the transfection reagent (µl):DNA mass (µg) was maintained at a 5:1 ratio, when the mastermix was produced it was adjusted to include an extra half a well to account for pipetting error and all transient transfections were undertaken in a six well plate (Corning).

In the production of a mastermix, a calculated volume of serum free DMEM at room temperature was pipetted into a sterile eppendorf. Then 4 µg of DNA was added and the DNA-DMEM suspension agitated. This was incubated at room temperature for 5 minutes as per the manufacture's protocol. Then a defined volume of Viafect transfection reagent was added drop-wise with continual agitation of the suspension and incubated at room temperature for 15 minutes. Post incubation, the transient transfection mixture was added to the well in a dropwise circular motion to ensure maximum cell coverage. Notably, this was also performed alongside a 'Mock' condition in which cells were incubated in the presence of Viafect and DMEM in the absence of DNA, as a control.

Due to the non-toxic nature of Viafect transfection reagent a media change was not necessitated post transfection. Cells were incubated for 72 hours prior to harvesting for total protein lysate.

Protein Extraction and Quantification:
Materials
Sterile PBS: 1 PBS Tablet (Gibco) dissolved in 500 ml of ddH20. This was either autoclaved or filtered with a 0.22 µM filter, with Class II Lamina flow hood.
PAPBNI Buffer: NaCl 0.15M, HEPES 0.05M, NP-40.1%, Sodium Deoxycholate (SOC) 0.5%, SDS 0.10%, EDTA 0.01M, Protease Inhibitor tablet 1 in 50 ml (Roche). This was aliquoted into 5 mls, and stored at −20.
Cells Scrappers (Invitrogen)
Eppendorfs
Benchtop Microcentrifuge
DC Assay Protein kit: Reagent A, S and B (BioRad).
2 µg BSA Standard (Invitrogen)
96 Well plate (Corning)
96 Well plate reader (Genbank)
Protein Extraction:

Post 72 hour incubation, growth media was aspirated, cells were washed with 500 µl ice cold PBS and 100 µl PABPN1 RIPA Buffer added. The cells were then scrapped down to the bottom of the well, with the plate held at a 45° angle, before being incubated at 4° C. on ice for 5 minutes. The samples were then transferred to pre-chilled and labelled eppendorfs, prior to being vortexed every 30 seconds for a further 15 minutes. The resultant protein lysates were then centrifuged at 13,000 rpm for 15 minutes, in a benchtop microcentrifuge to allow cell debris to pellet. The supernatant was then transferred to a fresh pre-chilled and labelled 0.5 ml screw top tube, and stored at −20° C.

Protein Quantification:

A defined dilution series of BSA in the protein extraction PABPN1 Buffer is prepared providing concentrations ranging from 0-2 µg of BSA respectively. As shown below:

| Conc (µg)   | 2  | 1.8 | 1.5 | 1.2 | 1  | 0.8 | 0.6 | 0.4 | 0.2 | 0  |
|-------------|----|-----|-----|-----|----|-----|-----|-----|-----|----|
| RIPA buffer | 0  | 4   | 10  | 16  | 20 | 24  | 28  | 32  | 36  | 40 |
| BSA         | 40 | 36  | 30  | 24  | 20 | 16  | 12  | 8   | 4   | 0  |

These protein standards were loaded at a volume of 0.5 µl, alongside extracted protein samples at a volume of 5 µl in a 96 well plate. All samples were loaded in triplicate to assert the accuracy/ensure reliability of the resulting absorption readings obtained.

In the fume hood: Reagent A +S (1 ml of A to 20 µl of S) was added at volume of 25 µl to each of the samples from a low to high concentration wherever possible; this being a precautionary measure to prevent contamination. Subsequently, 200 µl of Reagent B is applied and the resultant mixture is agitated and incubated for 15 minutes at room temperature. A colorimetric analysis is undertaken at 750 nm using the (Gen) 96 well plate reader. The absorption readings were then, used to calculate an average protein concentration of the three samples from the standard curve.

Western Blotting

Materials

NuPage 10× Reducing Agent (ThermoFischer)
NuPage 4× Loading Dye Sample (ThermoFischer)
NuPage 3-8% Tris Acetate precast gradient gels (ThermoFischer)
NuPage Antioxidant (ThermoFischer)
Prestained HiMark Ladder (Life technologies)
NuPage 3-8% Tris Acetate Running Buffer (ThermoFischer)
NuPage 20× Transfer Buffer (ThermoFischer)
Absolute Methanol (VWR)
I-Cell Blot Tank (Thermo Fischer)
0.45 μM Nitrocellulose membrane (GE Healthcare)
Ponceau Stain (ThermoFischer)
Filter paper
Marvel Milk Powder
Tween 20 Detergent (Sigma)
ECL solution 1 and 2 (Promega)
Amersham Hyperfilm 18 cm×24 cm (GE Healthcare)
Odyssey SA (Licor)
Antibodies

| Primary Antibodies | | | |
|---|---|---|---|
| Antibody name | Raised in | Dilution Used | Binds to |
| 6C5 (Dr. Glenn Morris) | Mouse | 1 in 100 | 17a.a C-Terminal |
| MannEx 1011C (Dr. Glenn Morris) | Mouse | 1 in 100 | Hinge/Spectrin repeats (Exon 10-11) |
| Tubulin (Abcam 40774) | Rabbit | 1 in 2500 | Alpha Tubulin Subunit |

| Secondary Antibodies | |
|---|---|
| Antibody name | Dilution Used |
| Goat α Mouse (Green Fluorescence) (LI-COR) | 1 in 10000 |
| Donkey α Rabbit (Red Fluorescence) (LI-COR) | 1 in 10000 |

Sample Preparation

Samples of total protein lysate were produced in a 4× master mix, this was to allow repetitions with antibodies if required. Typically a 4×40 ul master stock would contain 200 μg total protein. Samples were then prepared in a 1.5 ml screw top tube with: 4 μl Reducing Agent, 10 μl of Loading Sample Dye and the remaining volume is supplemented with ddH20. The samples were prepared alongside a positive control, either dystrophin extracted from muscle or from a previous positive transfection. Then denatured by heating to 70° C. for 10 minutes.

Gel Preparation and Electrophoresis

A 3-8% Tris-Acetate precast gradient gel (ThermoFischer) was used to resolve the full length dystrophin protein. In preparation of the gel, the comb was removed and wells washed with ddH20. In addition, a white adhesive strip sealing the foot of the gel was removed. Gels were then placed in the I-Cell Blot tanks vertically. Then a 10 μl aliquot of the 4× master stock of each protein sample was loaded alongside, a pre-stained Hi-Mark ladder (Life Technologies). The surrounding tank was filled approximately 1 cm from the top, with 1× 3-8% Tris-Acetate buffer and 500 μl of antioxidant was applied immediately prior to the initiation of electrophoresis. The gel was run for approximately 1 hour and 15 minutes at 150V, in accordance with the Nupage technical guide. The blue loading dye reaching the 'foot' of the gel and the ladder separation were parameters by which sufficient separation was assessed. During this time blotting pads were soaked in 1× transfer buffer: supplemented with 10% methanol and 1 ml antioxidant. Filter paper and 0.45 μM nitrocellulose membranes were cut to correct size for the transfer.

Electro-Transfer to Nitrocellulose Membrane.

Upon suitable separation of the ladder and by extension the proteins; the Nupage Electro-transfer cassette was prepared in accordance with the protocol (see NuPage Technical guide 2013).

Once pre-soaked blotting pads were applied to the bottom of the electro-transfer cassette, the 3-8% Tris acetate gels cases were 'cracked' open to liberate the polyacrylamide gels. The top of the gel, above the top band of the Hi-Mark ladder was removed and disregarded. The remainder of the gel was floated, using the buffer, to be situated above filter paper, lifted out of the transfer buffer and placed to the transfer cassette. Once performed, the 0.45 μm nitrocellulose membrane was submersed in buffer and placed on top. This was then rolled across the surface of the gel using a plastic roller to ensure tight contact throughout. A filter paper and a blotting pad placed on top. The whole cassette was kept wet during this time. If a second gel was present then the process was repeated. When completed this was placed in the I-Cell tank. The top of the electro-transfer cassette was refilled with 1× transfer buffer and the surrounding area filled with cold ddH20. The proteins were then transferred for 2 hours at 30V.

Post-Transfer Checks and Blocking

Following the two hour transfer, the membrane was stained with 1× Ponceau. This stains all proteins across the lanes and is used to ensure that the transfer was complete and successful. The stain was then washed off with 0.1% PBS-T, washing at 5 minute intervals until no stain was visible.

The nitrocellulose membrane was then blocked with 5% Marvel milk in 0.1% PBS-T for 1 hour at room temperature, to prevent non-specific binding. Once the membrane was blocked, the membrane was cut in half between the 55 and 71 kDa HiMark Ladder bands. The top piece of 0.45 μM nitrocellulose was incubated at 4° overnight in a 1 in 100 dilution of 6C5 or MannEx10-11c and the bottom a 1 in 2500 dilution of Rabbit Anti-tubulin.

Visualisation of the Nitrocellulose Membrane Using the Odyssey

Following overnight incubation with primary antibodies, 4 washes in 0.1% PBS-T was undertaken for 5 minutes. The secondary antibodies, which are conjugated to a fluorescent label were diluted to 1 in 10,000. The nitrocellulose membrane was then incubated for a further hour, prior to the repetition of 4 washes for 5 minutes in 0.1% PBS-T. This was then scanned at 700 nm and 800 nm channels respectively, using the Odyssey SA machine (Li-Cor). Dystrophin would be present within the 800 nm channel and the α-tubulin present within the 700 nm channel.

Quantification of Dystrophin

Software

ImageStudios Version 4 (Li-Cor)

Methods

The nitrocellulose membrane was then visualised with Image Studios Version 4. Bands were automatically identified using the software, and adjusted to be tight to the band in question in individual 800 nm and 700 nm channels. User defined noise values were subtracted away from the band in question and used to attain intensity values, for both dystrophin (800 nm) and α-tubulin (700 nm). The values were normalised to tubulin:

$$\frac{\text{Dystrophin Fluorescence Intensity}}{\alpha - \text{Tubulin Fluorescence Intensity}} = \text{Normalised Values}$$

This was performed for each lane and the native and optimised dystrophin (n=5) and a mean value was attained. Once mean values were attained the Sequence optimised dys/tub ratio was normalised to the native dys/tub, to establish a fold difference in expression.

Results

Initial Assessment of Dystrophin Expression from Native and Optimised, GFP Tethered Dystrophin Constructs:

Initially, a visual indication of whether sequence optimisation improves transcription and subsequently synthesis of recombinant dystrophin protein was sought. In pursuit of this plasmids containing native and optimised full-length dystrophin cDNA (SEQ ID NO: 1) directly tethered to eGFP were transiently transfected into Hek293T culture. Plasmids were driven by the Cytomegalovirus (CMV) promoter, a strong viral promoter to ensure higher levels of protein expression. The direct tethering of eGFP to dystrophin enables fluorescence to be used as an indicator of dystrophin expression; particularly, as the stoichiometry of eGFP:dystrophin is equivalent in the resultant fusion protein.

Both full-length native and optimised dystrophin plasmids were transfected at a 4 µg dose to Hek293T using a 5:1 transfection reagent:DNA ratio. Cultures were then subject to microscopy imaging at 24, 48 and 72 hours post transfection; the latest time point in this series, being reflective of the time taken for dystrophin protein to accumulate, to optimal levels for detection by western blotting.

Figure 1:
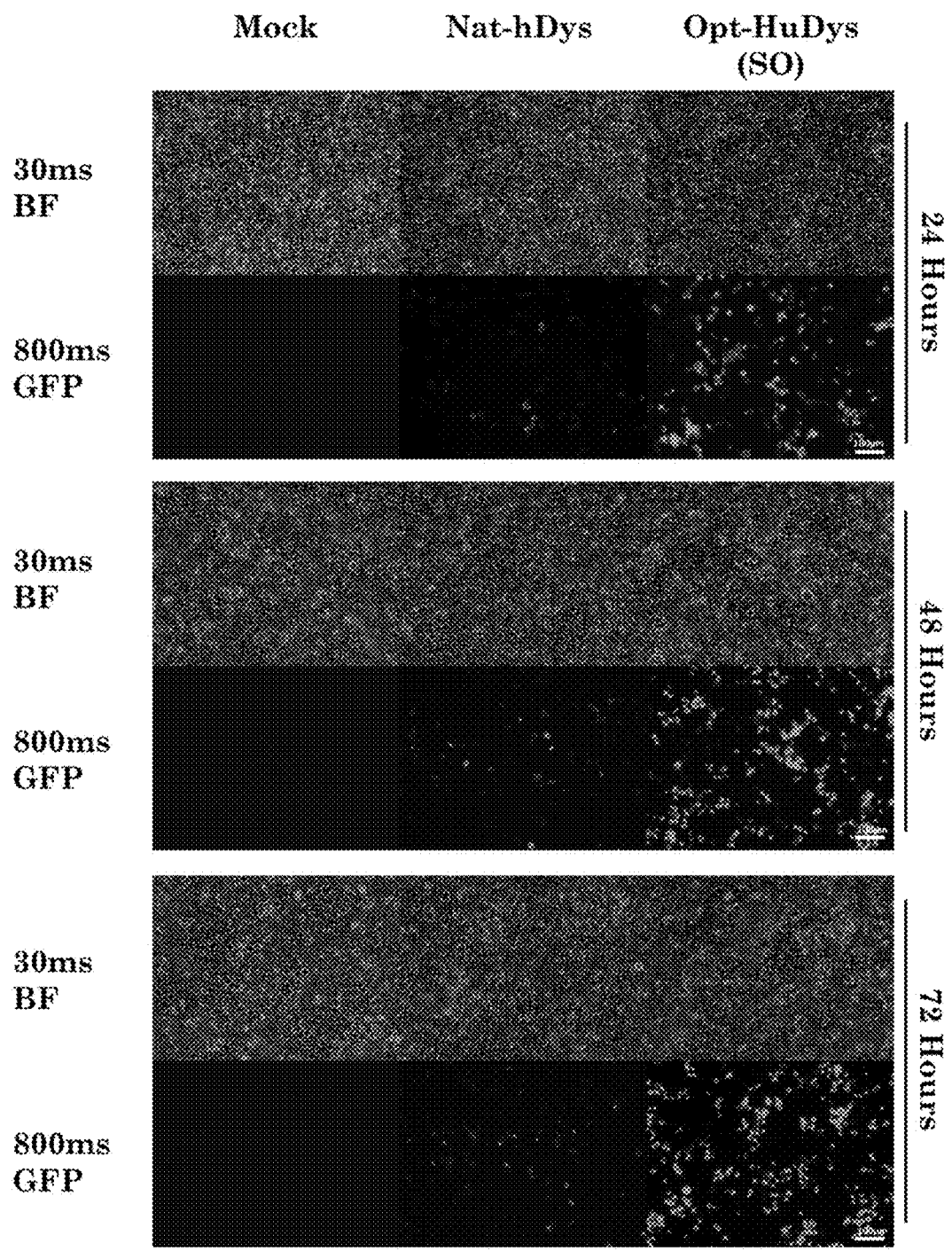
FIG. 1: Visual demonstration that sequence optimisation of cDNA improves recombinant protein expression as demonstrated by using constructs encoding native and optimised, full-length dystrophin tethered to eGFP. Hek293T cells transfected with native and sequence optimised full-length dystrophin-eGFP constructs, Nat-hDys and Opt-HuDys (SO) respectively. Transient transfections were undertaken at 4 µg with a 5:1 viafect reagent:DNA ratio. Subsequent GFP expression was imaged at sequential time points of 24, 48 and 72 hours with the Zeiss microscope at 10× magnification and 30 ms BF and 800 ms GFP channel exposures. A noticeable accumulation of green fluorescence can be seen in sequential time points for both constructs; in addition a difference in fluorescence intensity is seen between native and optimised dystrophin encoding constructs.

There was an apparent difference in green fluorescence, observed between native and optimised cultures post-transfection, across all time points examined Initially, the number of GFP positive cells in the culture, indicated successful transfection of both native and optimised constructs. Moreover, the intensity of fluorescence appears to increase from 24-72 hour time points irrespective of optimisation; likely attributable to the accumulation of dystrophin-eGFP transcript and subsequent protein synthesis. However, there was a striking increase in fluorescence intensity, observed in the optimised dystrophin culture relative to the native, at all time points examined (FIG. 1). This was suggested to be due to the sequence optimisation of the plasmid. The proposed implication being that the optimised construct enhances transcriptional efficiency and subsequently dystrophin-eGFP protein synthesis.

Quantifying the Difference in Expression of Native and Optimised Dystrophin Constructs Driven by a CMV Promoter:

The increased fluorescent intensity observed, prompted direct assessments of dystrophin protein expression for both CMV driven Nat-hDys and Opt-HuDys (SO) constructs. It was resolved that constructs without the GFP tag should be used in this examination. Transient transfections of plasmids were repeated at 4 µg utilising the 5:1 viafect transfection reagent:DNA ratio previously described. Cultures were incubated for 72 hours post transfection and lysed for total protein; this being in line with optimal accumulation of dystrophin protein. The samples were subsequently quantified and screened with two dystrophin antibodies: The 6c5 antibody, which binds to the carboxyl C-terminus of the dystrophin protein and the MannEx1011c, which binds to a dystrophin protein epitope, encoded between exons 10 and 11. This was performed prior to subsequent visualisation and quantification against an alpha-tubulin loading control using the Odyssey Licor system.

Figure 2:
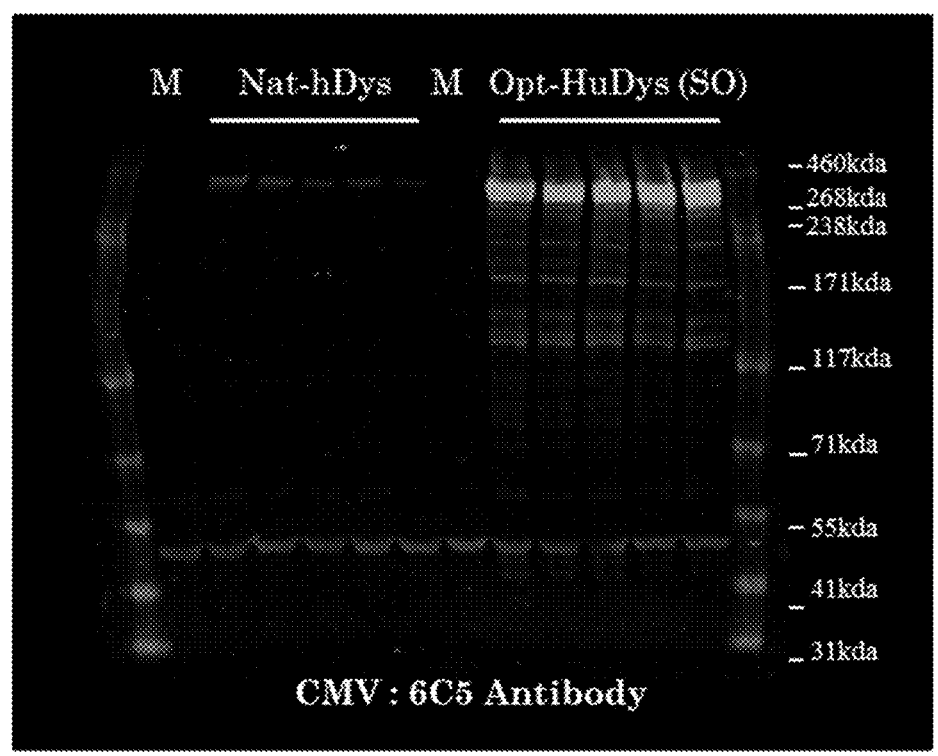
FIG. 2: Optimisation of cDNA sequence increases recombinant dystrophin expression. Plasmids expressing native (Nat-hDys) and sequence-optimised dystrophin (Opt-HuDys-SO) cDNAs from the CMV promoter were transfected into HEK293 cells (n=5). After 72 h cultures were harvested and processed for Western blotting (A) 50 µg total protein lysate was analysed with antibodies to dystrophin (6C5) and alpha-tubulin. Dystrophin bands were then quantified relative to the alpha-tubulin loading controls and mean intensity ratios plotted (B: mean±SEM: ***8 $p<0.001$ (unpaired t-test). Sequence optimisation produced a 57-fold increase in expression.
Figure 2:
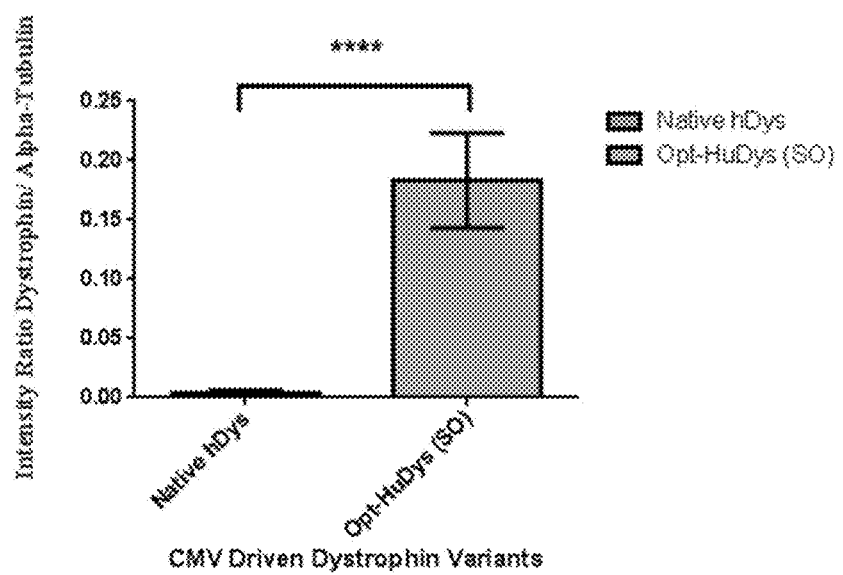
Figure 3:
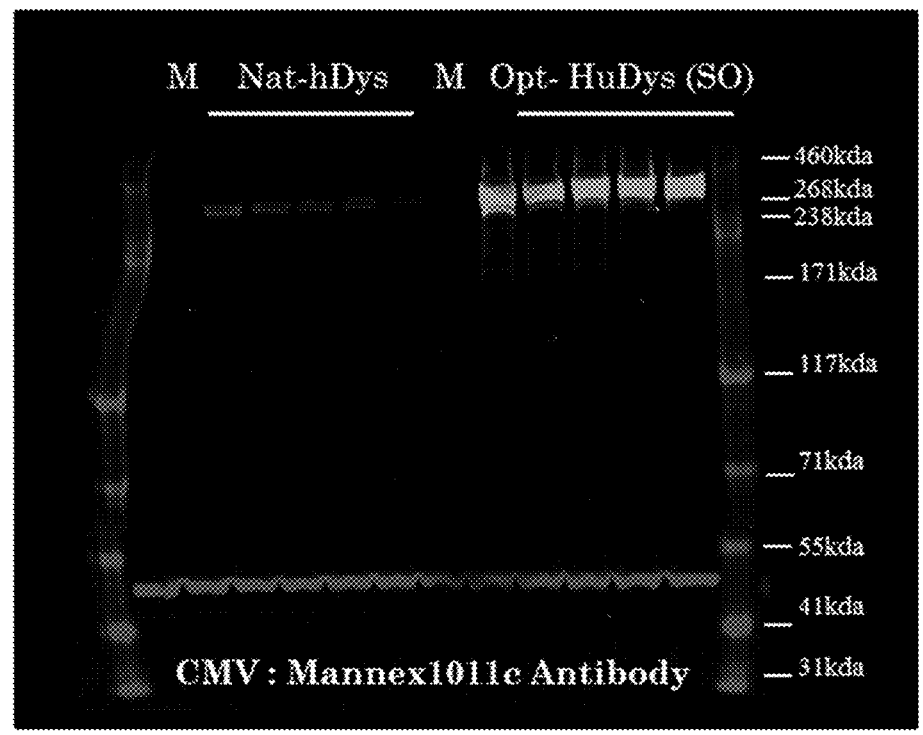
FIG. 3: Optimisation of cDNA sequence increases recombinant dystrophin expression. Plasmids expressing native (Nat-hDys) and sequence-optimised dystrophin (Opt-HuDys-SO) cDNAs from the CMV promoter were transfected into HEK293 cells (n=5). After 72 h cultures were harvested and processed for Western blotting (A) 50 µg total protein lysate was analysed with antibodies to dystrophin (ManEx1011c) and alpha-tubulin. Dystrophin bands were then quantified relative to the alpha-tubulin loading controls and mean intensity ratios plotted (B: mean±SEM: *** $p<0.001$ (unpaired t-test). Sequence optimisation produced a 22-fold increase in expression.
Figure 3:
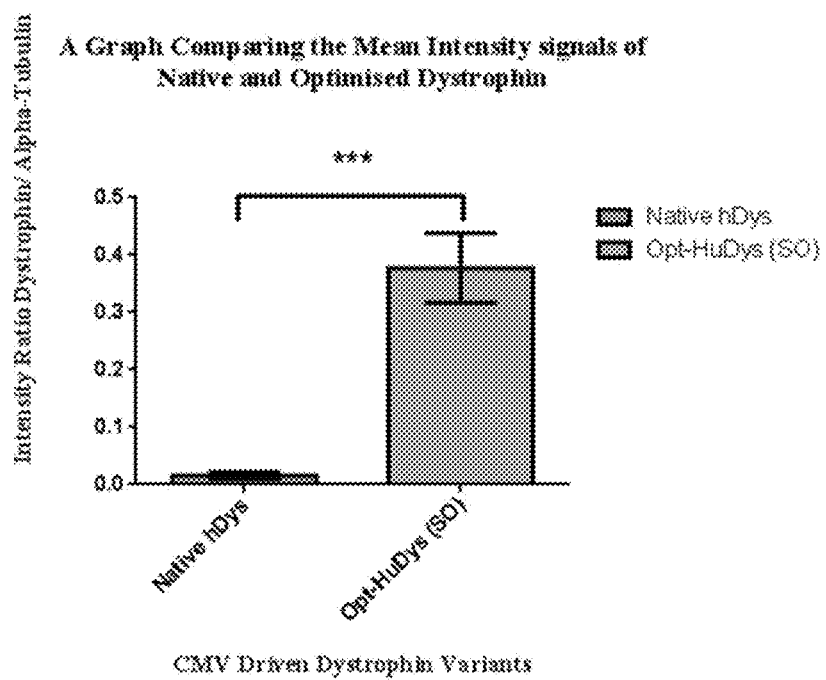

Importantly both constructs Nat-hDys and Opt-HuDys (SO), expressed a 427 kDa protein as determined by a HiMark Nupage Ladder, consistent with full-length dystrophin. This was detected with both the 6C5 and the MannEx1011c antibodies. Congruent with the previous investigation, the sequence optimised construct yielded a larger area band with increased intensity relative to the native. This trend was retained across 5 samples that were transiently transfected (FIG. 2 and FIG. 3). During the quantification, dystrophin fluorescence in the 800 channel was divided by tubulin in the 700 channel and a mean of Opt-HuDys-SO ratios attained were normalised to that of Nat-Dys. This form of analysis indicated a striking 57-fold difference with 6C5 antibody and a 22-fold difference with the MannEx101c antibody. This was deemed statistically significant in both cases giving a p=>0.001 by an unpaired t-test.

Additionally, it should be emphasised that on examination of the western blot an alternative banding pattern between the two antibodies was observed. The 6C5 antibody appeared to produce a characteristic laddering pattern in the Opt-HuDys (SO) construct that was not observed in the case of the Nat-hDys construct. The additional banding seen had moderate intensity comparable to the full-length band. In contrast the Mannex1011c antibody resulted in a singular sharp band for both Nat-hDys and Opt-HuDys (SO) constructs, with few additional bands at low intensity. In the case of the latter, this is likely the result of increasing the brightness to visualise the Nat-hDys bands.

Quantifying the Difference in Expression of Native and Optimised Dystrophin Constructs Driven by a Spc512 Promoter:

In the first series of investigations, CMV driven constructs were used. However, in the context of translational application, a muscle specific promoter would be advantageous in providing expression localised to muscle (Counsell J R et al., Sci Rep. 7:44775 (2017) and Meng, J. et al., Scientific Reports, 6(1), p. 19750 (2016)). In examination of this, Nat-Dys and Opt-Dys-SO constructs driven by the muscle specific Spc512 promoter, were transiently transfected at a 4 µg dose and protein harvested at 72 hours. Protein samples were prepared, subject to western blot and quantified in a manner consistent with the CMV based experiments.

Figure 4:
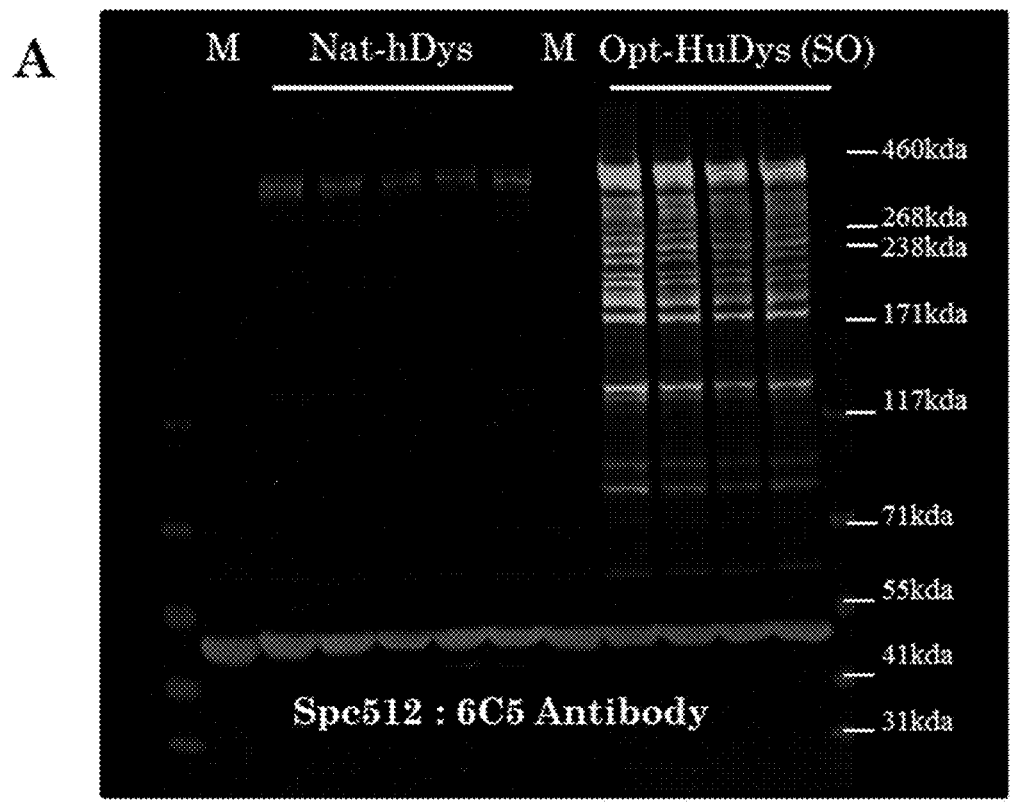
FIG. 4: Optimisation of cDNA sequence increases recombinant dystrophin expression. Plasmids expressing native (Nat-hDys) and sequence-optimised dystrophin (Opt-HuDys-SO) cDNAs from the Spc512 promoter were transfected into HEK293 cells (n=5). After 72 h cultures were harvested and processed for Western blotting (A) 50 µg total protein lysate was analysed with antibodies to dystrophin (6C5) and alpha-tubulin. Dystrophin bands were then quantified relative to the alpha-tubulin loading controls and mean intensity ratios plotted (B: mean±SEM: ***8 $p<0.001$ (unpaired t-test). Sequence optimisation produced a 15-fold increase in expression.
Figure 4:
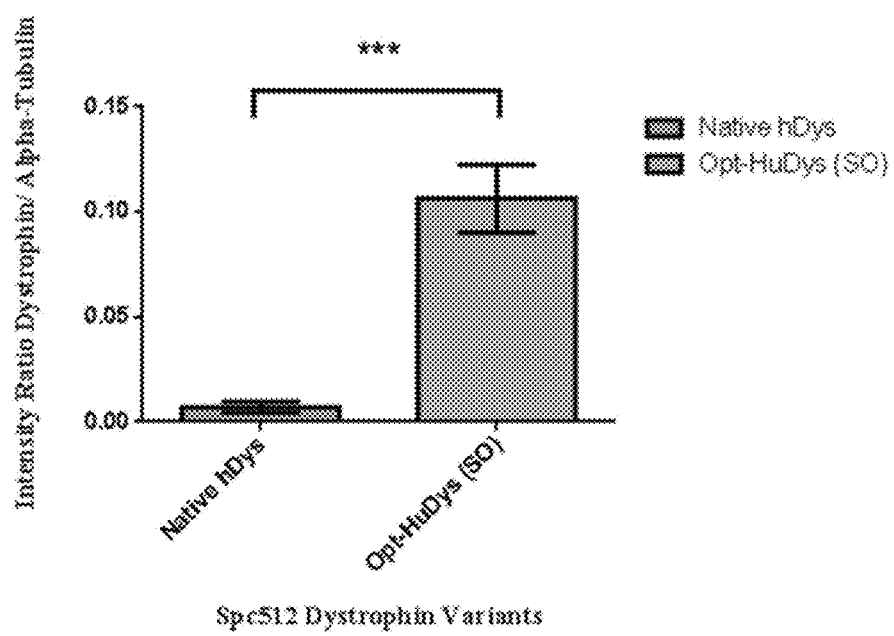
Figure 5:
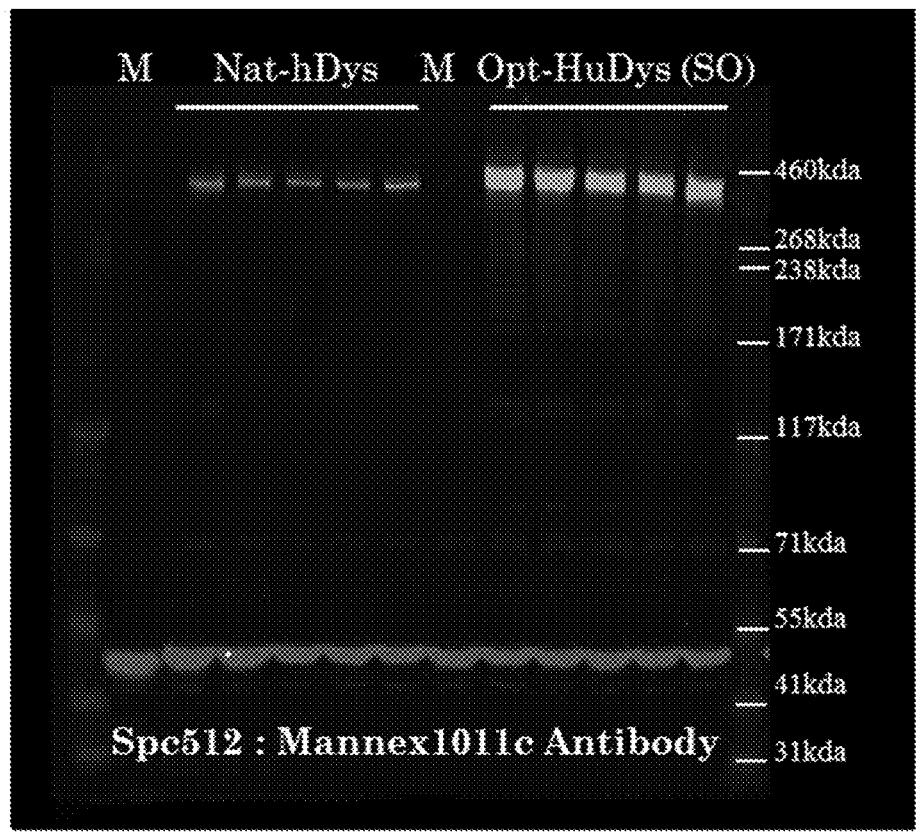
FIG. 5: Optimisation of cDNA sequence increases recombinant dystrophin expression. Plasmids expressing native (Nat-hDys) and sequence-optimised dystrophin (HuDys-CO) cDNAs from the Spc512 promoter were transfected into HEK293 cells (n=5). After 72 h cultures were harvested and processed for Western blotting (A) 50 µg total protein lysate was analysed with antibodies to dystrophin (ManEx1011c) and alpha-tubulin. Dystrophin bands were then quantified relative to the alpha-tubulin loading controls, and mean intensity ratios plotted (B: mean±SEM: **** p<0.0001 (unpaired t-test). Sequence optimisation produced a 17-fold increase in expression.
Figure 5:
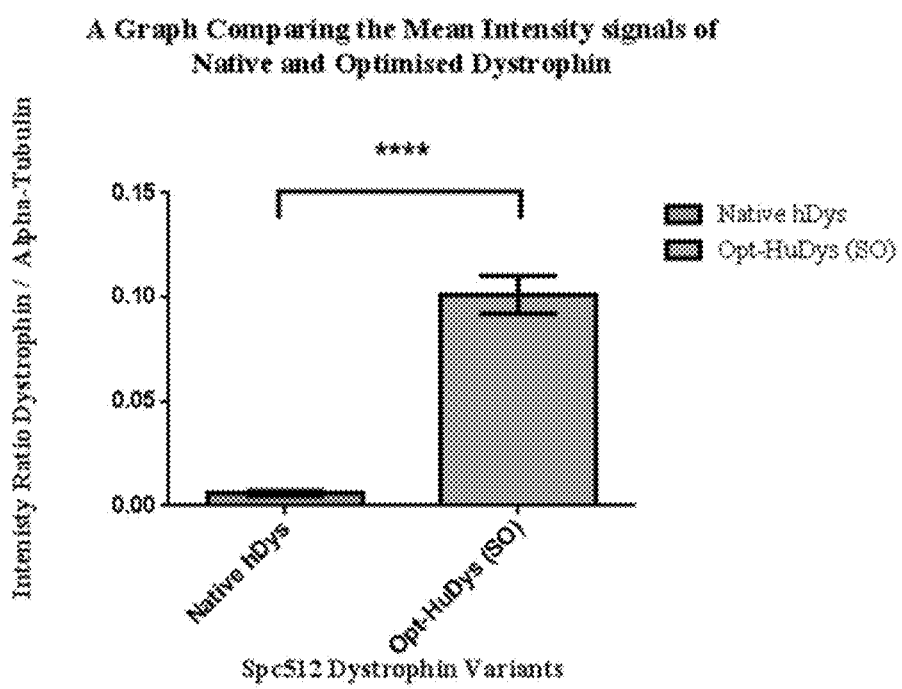

The Opt-Dys-SO construct once again resulted in a protein band of a greater area with an increased fluorescent intensity, relative to Nat-Dys with 6C5 and ManEx1011c antibodies (FIG. 4) and (FIG. 5). In this instance a 15-fold difference and a 17-fold difference were determined respectively. Notably, the difference whilst less prominent than observed with the CMV driven constructs, is still present. Finally, the laddering effect previously observed with the 6C5 antibody, is retained even with the use of an alternative promoter. This finding was somewhat unexpected due to the use of the Spc512 muscle-specific promoter, but was attributed to the Hek293T cell culture enabling 'leaky expression'.

Design of an Exogenous Repair Template:

The exogenous repair template was designed with numerous features to make it optimal for this investigation. Firstly, it included a backbone sequence amenable to the cloning of multiple dystrophin cDNA variants, including the full-length optimised sequence. Secondly, a splice acceptor was appended at the 5' end, in place of a promoter. Moreover, the presence of the 5' splice acceptor would enable the endogenous Dp427m promoter and indeed other full-length promoters to splice to the exogenous repair template. As a consequence, the resultant protein will have the correct spatial and temporal expression patterns. It is hypothesised that this will ameliorate a range of pathogenic disease causing mutations across the DMD gene.

To attain a backbone sequence amenable to the cloning of a variety of dystrophin cDNA transgenes, all unique restriction endonucleases were identified across full-length Opt-HuDys (SO). This served to identify two unique restriction sites. At the 5' end this was FseI, present 30 nucleotides into exon 6 and at the 3' end NotI situated at the terminus of exon 79. Thus a sequence was constructed with: DMD cDNA of exons 2-6 upstream of an FseI site, an intervening cyan fluorescent marker sequence and finally, a NotI site. It was determined that this sequence would enable directional cloning of the sequence optimised dystrophin variant.

In construction of an Exon 2-6 DMD cDNA block, consensus sequences of exons 1-6 of the Dp427m isoform, were aligned against full-length sequence optimised dystrophin cDNA. In this manner exons 1-6 of sequence optimised dystrophin cDNA, was identified. Exon 1, determined as the first 31 nucleotides of the sequence, was subsequently removed (Koenig et al., *Cell*, 50(3), pp. 509-17 (1987)). It was anticipated that these nucleotides would be reconstituted by the endogenous Dp427m promoter, if successful splicing to a delivered dystrophin transgene occurred. To this purpose, exon 2 was flanked at the 5' end with a human β-globin synthetic splice acceptor, and other regulatory sequences to facilitate splicing, including: a polypyrimidine tract and synthetic branch points (Seth et al., *The Journal of biological chemistry*, 283(15), pp. 10058-67 (2008); Popplewell et al., *Human gene therapy*, 24(7), pp. 692-701 (2013)). These sequences were modified to include a silent mutation, to generate a HpaI restriction site and identified as a strong splice acceptor by human splice finder (Desmet et al., *Nucleic acids research*, 37(9), p.e67 (2009)). Thus this splice sequence was selected to facilitate the splicing of the endogenous promoter to the integrated dystrophin transgene. Moreover, the inclusion of the HpaI restriction site would enable this sequence to be replaced with a native sequence with ease should this be required.

The 3' end of this cDNA block, downstream of the NotI site, was also flanked by a sequence indicated to improve transcription in lentiviral vectors; this being a mutated Woodchuck Hepatitis Virus Post-transcriptional regulatory element (mWPRE) fused to a polyA (Ranzani et al., Nat Methods. 10(2):155-61 (2013)).

Between these FseI and NotI sites, a Cyan fluorescent protein (CFP) was encoded. The sequence was modified to remove the initiating methionine and append the first two nucleotides of DMD exon 2. This was undertaken to retain the open reading frame of partial Dys-CFP fusion protein and reduce background fluorescence that may arise from aberrant firing of the methionine. This was anticipated to provide the benefit of a visual blue-fluorescent output, which could be used to indicate Dys-CFP transgene integration and track subsequent enrichment processes. It was anticipated that this would streamline the development of integration methods, in Hek239T and patient myoblast cultures. Moreover, the intervening CFP sequence could be used as a spacer within the DMD intron 1 repair template. The presence of a 491 bp band, removed upon FseI and NotI double digest could be used to indicate successful cleavage of the repair template and facilitate sub-cloning of dystrophin cDNA variants.

Due to the HDR pathway occurring with relatively low efficiency, an antibiotic selection cassette, SV40-Zeocin-PolyA, was placed downstream of the WPRE and PolyA sequences. This encodes the She Ble protein, which when expressed renders the zeocin antibiotic inactive (Hockemeyer et al., *Cell stem cell*, 3(3), pp. 346-353 (2008)). This sequence was modified to include a silent point mutation to remove a FseI site present. This ensured the unique core FseI and NotI sites required for directional sub-cloning of dystrophin variants was retained.

The zeocin selection cassette was resolved upon, as during immortalisation process of patient myoblasts, harbouring the deletion of exons 45-52 (445-52); they were rendered resistant to puromycin and neomycin antibiotics (Mamchaoui K. et al., *Skeletal muscle*, 1, p. 34 (2011)). Importantly, the cassette was floxed with LoxP sites that can conditionally remove intermediate sequences, in the presence of Cre-recombinase. Inclusion of the sequences of the LoxP sites was necessitated as post-enrichment of cells with successful integration; continued expression of the She Ble protein is undesirable. This is due to concerns that if cellular material is used to treat patients, in an ex-vivo engraftment manner they may acquire antibiotic resistance, which would have implications on their endogenous flora (Marie et al., *The Journal of Gene Medicine*, 12(4), pp. 323-332 (2010)).

Once the sequences of all constituents were obtained, they were flanked with 1 kb arms of homology. These were derived from human DMD Intron 1 consensus sequence from NCBI. The 1 kb arms initiated 6 nucleotides upstream of guide 3 and downstream of guide 4; these being the most upstream and downstream of the CRISPR guides identified. The arms of homology were designed in this manner, as a single guide with the highest efficacy had not yet been identified. As a direct consequence of this, no guide sequences were encoded within the exogenous repair template. Thus circumventing the risk that the repair template may be cleaved or indeed dystrophin variants re-targeted upon integration into the genome, by the Cas9 system.

Once a full sequence of the human DMD intron 1 repair template was compiled, it was assessed in parallel with dystrophin variants and the ISceit-Lentiviral vector for common for non-cutters. The list of common non-cutters were examined for compatibility in a double digest setting and used to flank all components of the exogenous repair template. This sequence was used and the repair template in a Puc57 backbone was synthesised (FIG. 6). Finally, the sequence was inserted in reverse orientation into the ISciet lentiviral backbone; this was performed to maintain the viral mRNA structure and prevent aberrant splicing or termination occurring (FIG. 7).

Sub-Cloning the Optimised Full-Length Dystrophin cDNA into the Puc57 Intron 1 Exogenous Repair Template:

Following the synthesis of the Intron 1 exogenous repair template, focus was shifted to the sub-cloning of the optimised full-length dystrophin from Exon 6 to exon 79 between the FseI and NotI endonuclease restriction sites. To this purpose, the optimised full-length dystrophin was subject to a series of diagnostic digests to assert the identity of the construct. Once assured the construct digested in a manner consistent with that anticipated; both the destination vector Puc57-hINT1-RT and the optimised full-length dystrophin plasmids were subject to double digest with FseI and NotI restriction endonucleases. In the case of the destination vector the double digest served to remove the CFP marker and leave a 6638 bps backbone. Whereas in the case of the optimised full-length dystrophin it enabled the cDNA insert of interest to be liberated. Samples were resolved by electrophoresis and subjected to overnight ligation, post gel purification. Subsequent ligation mixtures of insert and destination vector and a vector control, containing only digested backbone, were then subjected to standard heat shock transformation. The E. coli suspension was allowed to recover and plated onto ampicillin plates for an overnight incubation at 30° C. The vector control yielded no colonies, indicating that no self-ligation had occurred, likely attributable to the incompatible DNA termini resulting from the double digest. In contrast, the ligation mixtures yielded a high number of single colonies that could be picked and characterised. These results taken together serve to indicate that the optimised full-length dystrophin fragment from exon 6-79 was likely ligated into the destination vector backbone.

In an attempt to assess whether ligation was successful a colony PCR was undertaken. The primer pairs were designed for the colony PCR, so the forward primer was present within the Exon 2-6 region of the Puc57-hINT1-RT backbone upstream of the FseI cleavage site; whereas the reverse primer would only be present if the optimised full-length dystrophin insert was ligated. Thus the resultant amplicon was only anticipated to occur in instances where the optimised full-length dystrophin transgene had been successfully inserted into the Puc57-hINT1-RT destination vector. Amplification of the Spc512-HuDys (SO) plasmid was used as a positive control, the Puc57-hINT1-RT destination vector pre-digest and ligation served as a negative control.

The first 4 colonies from the colony PCR series were selected, grown as a starter culture, mini-prepped and subject to restriction digest. This was to further confirm presence and identity of the optimised full-length dystrophin transgene insert. Initially, the FseI and NotI double digest were performed on putative Puc57-hINT1-HuDys-RT constructs, alongside the parental Spc512-HuDys SO plasmid, which provided the insert. All four colonies gave the anticipated digest profile, alongside the Spc512-HuDys (SO) control plasmid.

Additionally, a diagnostic digest using the ScaI restriction endonuclease was undertaken. This produces distinct banding patterns for the parental Spc512-HuDys (SO) and the Pu57-hINT-HuDys-RT. Once again the four colonies gave the anticipated digest profiles, consistent with the optimised full-length dystrophin being inserted into the Puc57-hINT-RT. The above screens indicate a repair template carrying the optimised full-length dystrophin exons 2-79 and an independent selection cassette, all flanked by arms of homology was produced.

Discussion

Sequence Optimised Dystrophin cDNA:

Sequence optimisation of full-length dystrophin cDNA was shown to enhance protein expression relative to native controls. This was established by microscopy imaging and western blotting. Both studies utilised plasmid constructs under the control of a CMV promoter, with the first investigation using dystrophin variants directly tethered to eGFP. Importantly, in the case of full-length dystrophin, a 22-fold difference in protein expression was observed between native and optimised constructs. This large increase in protein expression from optimised cDNA from both experiments was striking.

The investigation was then extended to include optimised full-length dystrophin cDNA under the control of the Spc512 muscle restrictive promoter (Li et al., Nat Biotechnol. 17(3):241-5 (1999); Athanasopoulos et al., Methods Mol Biol. 709:21-37 (2011)). This was performed to examine whether the expression of Spc512 driven constructs could be compared in Hek293T cell culture. Importantly, the Spc512 promoter enabled full-length dystrophin expression in Hek293T cell culture; this is speculated to be due to this cell-line facilitating leaky expression of this promoter. Interestingly, native and optimised full-length dystrophin cDNA produced a varying fold difference in protein expression, when constructs were driven by the CMV and Spc512; being 22-fold and 15-17 fold respectively. This effect is attributed to two main parameters: the first being the relative strengths of the viral CMV and the muscle restrictive Spc512 promoters. Secondly, it was speculated that the expression of the full-length dystrophin cDNA may be reduced with the Spc512 promoter, due to its restrictive expression pattern.

The observations from both CMV and Spc512 studies together, could hold important implications for clinical translation. Numerous studies have provided an insight into the amount of dystrophin protein expression required relative to wild-type endogenous levels to ameliorate dystrophic pathology. Variable estimates have arisen, likely attributable to the nature of investigation from which estimates were derived and how dystrophin levels were quantified. Dystrophin expression of: 30% in BMD patients, 15% following antisense therapy in mice and finally, 20% in transgenic mice, were all shown to confer therapeutic benefit. Whilst estimates of therapeutic dystrophin expression vary between 15-30% among these investigations; they agree a uniform dystrophin expression across the majority of myofibres, as opposed to a sporadic distribution provides greater functional improvement. In addition, they indicate that the level of dystrophin correction required to be therapeutic, will be influenced by the muscle pathology and disease progression of the patient seeking treatment. The striking increase in protein expression observed, with the use of sequence optimised cDNA encoding full-length dystrophin, and relative to its native counter-part could facilitate the attainment of such expression thresholds. By extension of this it is speculated they could greatly improve clinical outcomes and functional improvements observed in clinical trials.

The striking fold differences in protein expression observed between native and optimised constructs necessitate the examination of the potential effects of supra-physiological levels of dystrophin proteins. Importantly, others have demonstrated that overexpression of full-length dystrophin, of up to 50-fold higher than endogenous levels, was well tolerated (Chamberlain, Soc Gen Physiol Ser. 52:19-29 (1997); Phelps S F, Hum Mol Genet. 4(8):1251-8 (1995); Wells D J, Hum Mol Genet. 4(8):1245-50 (1995)). This level was shown to ameliorate dystrophic pathology with the absence of any detrimental effects.

Design of an Exogenous Repair Template:

The improved protein expression resulting from sequence optimised full-length dystrophin cDNA served to influence exogenous repair template design. This prompted the generation of a backbone that would enable the directional sub-cloning of sequence optimised full-length dystrophin cDNA, allowing the exogenous repair template to be trialed in integration experiments.

The exogenous repair template was designed to facilitate a Homology Directed Repair (HDR) outcome, at the human DMD intron 1 locus. It was designed with 1 kb arms of homology isogenic to the human genome, directly upstream and downstream of the region of homology identified. This length of isogenic sequence is deemed optimal for successful exploitation of HDR pathways. Extension of homology arms beyond this size only result in marginal increases of transgene integration. In addition, the repair template also includes a floxed zeocin cassette, to facilitate positive selection processes (Mulsant et al., Somat Cell Mol Genet. 14(3):243-52 (1988); Seth et al., *The Journal of biological chemistry*, 283(15), pp. 10058-67 (2008)). This would enable enrichment of corrected cells, which is important due to the low efficiency of the HDR process.

Importantly, as scientists' understanding of the DNA damage response (DDR) continues to evolve, so too does the manner in which DNA repair pathways are exploited to facilitate the integration of genetic material. Recent investigations have used NHEJ-DNA repair pathways to introduce genetic material (Maresca et al., Genome Res. 23(3): 539-46 (2013); Suzuki et al., Nature. 540(7631):144-149 (2016)). This strategy is reliant upon genomic target sites of the endonuclease TALEN or CRISPR, being encoded in reverse orientation directly adjacent to the transgene for which integration is desirable. The resultant in-situ cleavage of genome and exogenous repair template, facilitates the integration of the transgene independently of the HDR pathway (Suzuki et al., Nature. 540(7631):144-149 (2016)). Importantly, the exogenous repair template in this investigation was designed so components were flanked with endonuclease restriction sites. Thus it could be easily customised to facilitate exploration of such strategies with dystrophin cDNA.

CONCLUSIONS

A novel exogenous repair template was designed with restriction sites enabling the sub-cloning of full-length sequence optimised dystrophin cDNA. This design was founded upon the demonstration that sequence optimisation enhanced recombinant dystrophin protein expression. It was designed with 1 Kb arms of homology isogenic to sequences upstream and downstream of the CRISPR MIT guide designs, identified within human DMD intron 1. Furthermore, it encodes a floxed zeocin cassette to facilitate positive selection during HDR investigations.

SEQUENCES

SEQ ID NO. 1 is a codon optimised full-length dystrophin cDNA including a 3 bp "stop" codon (nucleotides 11,059-11,061).

SEQ ID NO. 2 is the amino acid sequence of the human native dystrophin protein.

SEQ ID NO. 3 is a codon optimised full-length dystrophin cDNA (nucleotides 7-11,064) including a 6 bp optimised Kozak sequence (nucleotides 1-6) and a 3 bp "stop" codon (nucleotides 11,065-11,067).

The invention claimed is:

1. A nucleic acid molecule comprising a nucleotide sequence encoding a functional dystrophin protein, wherein the nucleotide sequence has at least 95% identity to the sequence of SEQ ID NO: 1.

2. The nucleic acid molecule of claim 1, wherein the nucleotide sequence has at least 96% identity to the sequence of SEQ ID NO: 1.

3. The nucleic acid molecule of claim 1, wherein the nucleotide sequence has at least 97% identity to the sequence of SEQ ID NO: 1.

4. The nucleic acid molecule of claim 1, wherein the nucleotide sequence has at least 98% identity to the sequence of SEQ ID NO: 1.

5. The nucleic acid molecule of claim 1, wherein the nucleotide sequence has at least 99% identity to the sequence of SEQ ID NO: 1.

6. The nucleic acid molecule of claim 1, wherein the nucleotide sequence has the sequence of SEQ ID NO: 1.

7. The nucleic acid molecule of claim 1, wherein the nucleotide sequence encodes a functional human dystrophin protein.

8. The nucleic acid molecule of claim 1, wherein the nucleotide sequence encodes a functional dystrophin protein having the amino acid sequence of SEQ ID NO: 2.

9. The nucleic acid molecule of claim 1, wherein the nucleotide sequence encoding the dystrophin protein is between 11,025 and 11,085 nucleotides in length.

10. A nucleic acid molecule comprising at least exons 53 to 79 of a nucleotide sequence encoding a functional dystrophin protein, wherein the nucleotide sequence has at least 95% identity to the sequence of SEQ ID NO: 1.

11. A vector comprising the nucleic acid molecule of claim 1.

12. The vector of claim 11, wherein the vector is comprised of three AAV vectors, each containing a portion of nucleic acid molecule comprising a nucleotide sequence encoding a functional dystrophin protein, wherein the nucleotide sequence has at least 95% identity to the sequence of SEQ ID NO: 1, wherein following transduction of a cell with the three AAV vectors, the nucleic acid molecule is produced.

13. A vector according to claim 11, wherein the vector is Puc57-human DMD intron 1 plasmid repair template Puc57-hINT1-RT or lentiviral human DMD intron 1 plasmid repair template Lenti-hINT1-RT.

14. A host cell comprising the nucleic acid molecule of claim 1 or the vector of claim 11.

15. A pharmaceutical composition comprising the nucleic acid molecule of claim 1 or the vector of claim 11 and one or more pharmaceutically acceptable excipients.

16. A method of treating muscular dystrophy, the method comprising administering a therapeutically effective amount of the nucleic acid molecule of claim 1 or the vector of claim 11 to a patient suffering from a muscular dystrophy.

17. The method of claim 16, wherein the muscular dystrophy is selected from Duchenne muscular dystrophy (DMD), Becker muscular dystrophy (BMD) and cardiomyopathy.

18. The method of claim 16, wherein the muscular dystrophy is Duchenne muscular dystrophy (DMD).

19. A method for delivery of a nucleotide sequence encoding a functional dystrophin protein to a subject, which method comprises administering to the said subject the nucleic acid molecule of claim 1 or the vector of claim 11.

* * * * *

UNITED STATES PATENT AND TRADEMARK OFFICE
CERTIFICATE OF CORRECTION

PATENT NO. : 11,725,032 B2  
APPLICATION NO. : 16/770358  
DATED : August 15, 2023  
INVENTOR(S) : Dickson et al.

It is certified that error appears in the above-identified patent and that said Letters Patent is hereby corrected as shown below:

On the Title Page

Page 2, Column 1, Other Publications, Lines 3-4:  
Delete "Tranferring" and insert --Transferring-- therefor Signed and Sealed this  
Fifth Day of December, 2023

Katherine Kelly Vidal  
*Director of the United States Patent and Trademark Office*

SEQUENCE LISTING

```
<160> NUMBER OF SEQ ID NOS: 3

<210> SEQ ID NO 1
<211> LENGTH: 11061
<212> TYPE: DNA
<213> ORGANISM: Artificial sequence
<220> FEATURE:
<223> OTHER INFORMATION: Codon optimised dystrophin cDNA

<400> SEQUENCE: 1
atgctgtggt gggaggaagt ggaagattgc tacgagcgcg aggacgtgca gaagaaaacc      60
ttcaccaaat gggtcaacgc ccagttcagc aagttcggca agcagcacat cgagaacctg     120
ttcagcgacc tgcaggacgg cagaaggctg ctggacctgc tggaaggcct gaccggccag     180
aagctgccca agagaaggg cagcaccaga gtgcacgccc tgaacaacgt gaacaaggcc      240
ctgagagtgc tgcagaacaa caacgtggac ctggtcaaca tcggcagcac cgacatcgtg     300
gacggcaacc acaagctgac cctgggcctg atctggaaca tcatcctgca ctggcaggtc     360
aaaaacgtga tgaagaacat catggccggc ctgcagcaga ccaacagcga gaagatcctg     420
ctgagctggg tccgccagag caccagaaac taccccccagg tcaacgtgat caacttcacc     480
acctcttgga gcgacggcct ggccctgaac gccctgatcc acagccacag acccgacctg     540
ttcgactgga acagcgtggt ctgccagcag agcgccaccc agagactgga acacgccttc     600
aatatcgcca gataccagct gggcatcgag aagctgctgg atcccgagga cgtggacacc     660
acctaccccg acaagaaatc catcctgatg tacatcacca gcctgttcca ggtgctgccc     720
cagcaggtct ccatcgaggc catccaggaa gtggaaatgc tgcccagacc ccccaaagtg     780
accaaagagg aacacttcca gctgcaccac cagatgcact acagccagca gatcaccgtg     840
tccctggctc agggctacga gagaaccagc agccccaagc ccagattcaa gagctacgcc     900
tacacccagg ccgcctacgt gaccaccagc gacccccaca gaagcccatt ccccagccag     960
```

```
cacctggaag ccccccgagga caagagcttc ggcagcagcc tgatggaaag cgaagtgaac    1020
ctggacagat accagaccgc cctggaagag gtgctgtcct ggctgctgtc cgccgaggac    1080
acactgcagg cccagggcga gatcagcaac gacgtggaag tggtcaaaga ccagttccac    1140
acccacgagg gctacatgat ggacctgacc gcccaccagg gcagagtggg caacatcctg    1200
cagctgggca gcaagctgat cggcaccggc aagctgagcg aggacgaaga gacagaggtg    1260
caggaacaga tgaacctgct gaacagcaga tgggagtgcc tgagagtggc cagcatggaa    1320
aagcagagca acctgcacag agtgctgatg gatctgcaga accagaagct gaaagagctg    1380
aacgactggc tgaccaagac cgaggaacgg accagaaaga tggaagagga ccccctgggc    1440
cccgacctgg aagatctgaa agacaggtg cagcagcaca aggtgctgca ggaagatctg    1500
gaacaggaac aggtccgcgt caacagcctg acccacatgg tggtggtggt ggacgagagc    1560
agcggcgatc acgccaccgc cgctctggaa gaacagctga aggtgctggg cgacagatgg    1620
gccaacatct gccggtggac cgaggacaga tgggtgctgc tgcaggacat cctgctgaag    1680
tggcagagac tgacagagga acagtgcctg ttctccgcct ggctgagcga aaagaggac    1740 gccgtcaaca agatccacac caccggcttc aaggaccaga cgagatgct gagcagcctg    1800 cagaaactgg ccgtgctgaa ggccgatctg aaaagaaaa agcagtccat gggcaagctg    1860
tacagcctga gcaggacct gctgtccacc ctgaagaaca gagcgtgac ccagaaaacc    1920 gaggcctggc tggacaactt cgccagatgc tgggacaacc tggtgcagaa gctggaaaag    1980
agcaccgccc agatcagcca ggccgtgacc acaacccagc cctccctgac ccagaccacc    2040
gtgatggaaa ccgtgaccac tgtgaccacc cgcgagcaga tcctggtcaa acacgcccag    2100
gaagaactgc cccctccacc ccccagaag aaaagacaga tcacagtgga cagcgagatc    2160
agaaagcggc tggatgtgga catcaccgag ctgcacagct ggatcaccag atccgaggcc    2220
gtgctgcaga gccccgagtt cgccatcttc agaaagagg gcaacttctc cgacctgaaa    2280 gaaaagtga cgccatcga gagagagaag gccgagaagt tcagaaagct gcaggacgcc    2340
agccgctctg ctcaggctct ggtggaacag atggtcaacg agggcgtgaa cgccgacagc    2400
atcaagcagg ccagcgagca gctgaactcc agatggatcg agttctgcca gctgctgtcc    2460
gagagactga actggctgga ataccagaac aacatcattg ccttctacaa ccagctccag    2520
cagctggaac agatgaccac caccgccgag aactggctga gatccagcc caccaccccc    2580 agcgagccca ccgccatcaa gagccagctg aagatctgca aggacgaagt gaacagactg    2640
tctggcctgc agccccagat cgagaggctg aagattcagt ctatcgccct gaaagagaaa    2700
ggccagggcc ccatgttcct ggacgccgac ttcgtggcct tcaccaacca cttcaaacag    2760
gtgttctccg acgtgcaggc cagagagaaa gagctgcaga ccatcttcga caccctgccc    2820
cccatgagat accaggaaac catgagcgcc atcagaacct gggtgcagca gagcgagaca    2880
aagctgagca tcccccagct gagcgtgacc gactacgaga tcatggaaca gagactgggc    2940
gagctgcagg ctctgcagtc cagtctgcag gaacagcaga gcggcctgta ctacctgagc    3000
accaccgtga agagatgag caagaaggcc ccctccgaga tctccagaaa gtaccagagc    3060
gagttcgaag gatcgaggg cagatggaag aagctgtcct tcagctggt ggaacactgc    3120 cagaaactgg aagaacagat gaacaagctg cggaagatcc agaaccacat ccagacccctg    3180 aaaaagtgga tggccgaggt ggacgtgttc ctgaaagagg aatggcctgc cctgggcgac    3240
tccgagatcc tgaaaagca gctgaagcag tgcagactgc tggtgtccga catccagaca    3300
atccagccca gcctgaactc cgtgaatgag ggcggccaga agatcaagaa cgaggccgag    3360
```

```
cctgagttcg ccagcagact ggaaaccgag ctgaaagaac tgaataccca gtgggaccac    3420
atgtgtcagc aggtctacgc ccggaaagag cccctgaagg gcggcctgga aaagaccgtg    3480
tctctgcaga aagacctgtc cgagatgcac gagtggatga cccaggccga ggaagagtac    3540
ctggaaagag acttcgagta caagaccccc gacgagctgc agaaagctgt ggaagaaatg    3600
aagagggcca agaagaggc ccagcagaaa gaggccaaag tcaagctgct gaccgagtcc    3660
gtgaacagcg tgatcgccca ggcccctccc gtggctcagg aagccctgaa gaagaactg    3720 gaaacactga ccaccaacta ccagtggctg tgcaccagac tgaacggcaa gtgcaagacc    3780
ctggaagaag tgtgggcctg ctggcacgag ctgctgagct acctggaaaa ggccaacaag    3840
tggctgaacg aggtggaatt caagctgaaa accaccgaga acatccctgg cggcgctgaa    3900
gagatcagcg aggtgctgga cagcctggaa aacctgatga cacagcgag gacaaccccc    3960 aaccagatca gaatcctggc ccagacactg accgacggcg gcgtgatgga cgagctgatc    4020
aacgaggaac tggaaaacctt caacagccgg tggcgcgagc tgcacgagga agctgtgcgg    4080
agacagaaac tgctggaaca gtccatccag agcgcccagg aaaccgagaa gtccctgcac    4140
ctgatccagg aaagcctgac attcatcgac aagcagctgg ccgcctatat cgccgacaag    4200
gtggacgccg cccagatgcc acaggaagct cagaagatcc agtccgacct gaccagccac    4260
gagatcagcc tggaagagat gaagaagcac aaccagggca agaggccgc ccagagggtc    4320 ctgagccaga tcgacgtggc ccagaaaaaa ctgcaggacg tgtccatgaa gttcaggctg    4380
ttccagaagc ccgccaactt cgagcagaga ctgcaggaat ccaagatgat cctggatgaa    4440
gtgaagatgc atctgccagc cctggaaaca aagtccgtgg aacaggaagt ggtccagtcc    4500
cagctgaacc actgcgtgaa cctgtacaag agcctgtccg aagtgaagtc cgaggtggaa    4560
atggtcatca agaccggcag acagatcgtg cagaaaagc agaccgagaa ccccaaagaa    4620
ctggacgaga gagtgaccgc cctgaagctg cactacaacg agctgggcgc caaagtgaca    4680
gagcggaaac agcagctgga aaagtgcctg aagctgtccc gcaagatgcg gaaagaaatg    4740
aacgtgctga cagagtggct ggctgccacc gacatggaac tgaccaagag aagcgccgtg    4800
gaaggcatgc ccagcaacct ggactccgag gtggcatggg gcaaggccac ccagaaagag    4860
atcgaaaagc agaaggtgca cctgaagtcc atcaccgaag tgggcgaggc tctgaaaacc    4920
gtgctgggca agaaagaaac cctggtggaa gataagctga gcctgctgaa ctctaactgg    4980
atcgccgtga ccagcagagc cgaggaatgg ctgaatctgc tgctggaata tcagaaacac    5040
atggaaacct tgaccagaa cgtggaccac atcaccaagt ggatcatcca ggctgacacc    5100
ctgctggacg agtccgagaa gaagaaacct cagcagaaag aagatgtgct gaagagactg    5160
aaggctgagc tgaatgacat cagacccaag gtggacagca ccaggacca ggccgccaac    5220 ctgatggcca ccacggcga ccactgcaga aaactggtgg aaccccagat ctccgagctg    5280
aatcacagat cgccgccat cagccacaga atcaagacag gcaaggccag catccccctg    5340
aaagagctgg aacagttcaa cagcgacatc cagaagctgc tggaacccct ggaagccgag    5400
atccagcagg gcgtgaacct gaaagaagag gacttcaaca aggacatgaa cgaggacaac    5460
gagggcacag tgaaagagct gctccagaga gcgacaacc tgcagcagcg catcaccgac    5520
gagagaaagc gcgaggaaat caagatcaag cagcagctcc tgcagaccaa gcacaacgcc    5580
ctgaaggacc tgagatccca gaagaaaag aaggccctgg aaatcagcca ccagtggtat    5640
cagtacaaga gacaggccga cgacctgctg aaatgcctgg acgacatcga gaagaagctg    5700
```

```
gctagcctgc ccgagcccag ggacgagagg aagatcaaag aaatcgaccg ggaactgcag    5760
aagaagaaag aggaactgaa cgccgtccgc aggcaggccg agggcctgtc tgaagatggc    5820
gccgctatgg ccgtggaacc cacccagatc cagctgagca gagatggcg cgagatcgag     5880 agcaagttcg cccagttccg cagactgaac ttcgcccaga tccataccgt gcgggaagag    5940
acaatgatgg tcatgacaga ggacatgccc ctggaaatta gctacgtgcc cagcacctac    6000
ctgaccgaga tcacacacgt gtcccaggca ctgctgaaag tggaacagct gctgaatgcc    6060
cccgacctgt gcgccaagga cttcgaggat ctgttcaagc aggaagagag cctgaagaat    6120
atcaaggact ccctgcagca gtccagcggc agaatcgaca tcatccacag caagaaaaca    6180
gccgccctgc agagcgctac ccccgtggaa cgcgtgaagc tgcaggaagc actgagccag    6240
ctggacttcc agtgggagaa agtgaacaaa atgtacaagg accggcaggg cagattcgac    6300
agatccgtgg aaaagtggcg gagattccac tacgacatca agatcttcaa tcagtggctg    6360
acagaggccg agcagttcct gagaaagacc cagatccctg agaactggga gcacgccaag    6420
tacaagtggt atctgaaaga actgcaggat ggcatcggcc agagacagac cgtggtccgc    6480
acactgaacg ccaccggcga agagatcatc agcagagca gcaagaccga cgccagcatc    6540
ctgcaggaaa agctgggctc cctgaacctg agatggcagg aagtgtgcaa gcagctgagc    6600
gacagaaaga aaaggctgga agaacagaag aatatcctga gcgagttcca gagggacctg    6660
aacgagttcg tgctgtggct ggaagaggct gacaatatcg cctccatccc cctggaaccc    6720
ggcaaagagc agcagctgaa agaaaaactg gaacaggtca aactgctggt ggaagaactg    6780
cctctgagac agggcagaat cctgaagcag ctgaacgaga caggcggccc tgtgctggtg    6840
tctgccccca tcagccccga ggaacaggac aaactggaaa acaaactgaa gcagacaaac    6900
ctgcagtgga tcaaggtgtc cagagccctg ccagagaagc aggggagat cgaggcccag    6960 atcaaggacc tgggccagct ggaaaaaaag ctggaagatc tggaagaaca gctcaaccat    7020
ctgctgctgt ggctgagccc catcagaaac cagctgaaa tctacaatca gcccaaccag    7080
gaaggcccct tcgacgtcaa agaaaccgag atcgccgtgc aggctaagca gcctgacgtg    7140
gaagagatcc tgagcaaggg acagcacctg tacaaagaga gcctgccac ccagcccgtg    7200 aagcgcaaac tggaagatct gtccagcgag tggaaggccg tgaaccgcct gctgcaggaa    7260
ctgagagcca agcagcccga cctggccct ggcctgacaa caatcggcgc cagccccacc    7320
cagacagtga ccctggtcac acagcccgtg gtcacaaaag agacagccat cagcaagctg    7380
gaaatgccca gctccctgat gctggaagtg cccgccctgg ccgacttcaa cagagcctgg    7440
accgagctga ccgattggct gtctctgctg gaccaggtca tcaagtccca gcgcgtgatg    7500
gtcggcgatc tggaagatat caacgagatg atcatcaagc agaaagccac catgcaggac    7560
ctggaacaga ggcggcctca gctggaagaa ctgatcacag ccgcccagaa cctgaaaaac    7620
aagaccagca accaggaagc caggaccatc atcaccgaca gatcgagag gatccagaat    7680 cagtgggacg aagtgcagga acatctgcag aacagacgcc agcagctgaa tgagatgctg    7740
aaggacagca cccagtggct ggaagctaaa gaagaggctg aacaggtcct gggacaggcc    7800
agagccaagc tggaatcttg aaagagggc cctacaccg tcgacgctat ccagaagaag    7860
atcaccgaga caaaacagct ggccaaggac ctgcggcagt ggcagaccaa cgtggacgtg    7920
gccaacgacc tggctctgaa gctgctgcgg gactacagcg ccgacgacac cagaaaggtg    7980
cacatgatca cagagaacat caacgcaagt tggcggagca tccacaagag agtgtctgag    8040
cgcgaggctg cactggaaga gactcacaga ctcctgcagc agttccccct ggacctggaa    8100
```

```
aaattcctgg cttggctgac cgaggctgag acaaccgcca acgtgctgca ggatgccacc    8160
agaaaagaga gactgctgga agatagcaag ggcgtgaaag aactgatgaa gcagtggcag    8220
gacctgcagg gcgaaatcga ggctcacacc gacgtgtacc acaacctgga cgagaacagc    8280
cagaagattc tgagaagcct ggaaggcagc gacgacgccg tgctgctgca gcggagactg    8340
gacaacatga acttcaagtg gtccgagctg cgcaagaagt ctctgaacat cagatcccat    8400
ctggaagcca gcagcgacca gtggaagaga ctgcacctga gtctgcagga actgctggtc    8460
tggctgcagc tgaaggacga cgagctgagc agacaggccc ccatcggcgg cgatttcccc    8520
gccgtgcaga acagaacga cgtgcacaga gccttcaaga gagagctgaa acaaaagaa     8580 cccgtgatca tgagcaccct ggaaactgtg cggatcttcc tgaccgagca gccctggaa     8640 ggactggaaa agctgtacca ggaacccaga gagctgcccc tgaggaacg ggcccagaac     8700 gtgacccggc tgctgagaaa gcaggccgaa gaggtcaaca ccgagtggga aagctgaac     8760 ctgcactccg ccgactggca gagaaagatc gacgagacac tggaacgcct gcaggaactg    8820
caggaagcta ccgacgagct ggatctgaaa ctgcggcagg ctgaagtgat caagggcagc    8880
tggcagcccg tggggaccct gctgatcgac tctctgcagg accatctgga aaaagtgaag    8940
gccctgaggg gcgagatcgc tcctctgaaa gaaaacgtgt cccacgtgaa cgacctggcc    9000
aggcagctga ccacccctggg catccagctg tccccctaca acctgagcac tctggaagat    9060
ctgaacacca gatggaagct gctgcaggtc gccgtggaag atagagtgcg gcagctgcac    9120
gaagcccaca gagacttcgg ccctgcctcc cagcacttcc tgtccacaag cgtgcagggc    9180
ccctgggaga gggccatcag ccctaacaag gtgccctact acatcaacca cgagacacag    9240
accacctgtt gggaccaccc caagatgacc gagctgtatc agtctctggc cgacctgaac    9300
aatgtgcggt tcagcgccta cagaaccgct atgaagctga ggcgcctgca gaaagccctg    9360
tgcctggacc tgctgagcct gagcgccgcc tgtgacgccc tggaccagca caacctgaaa    9420
cagaatgacc agcccatgga tatcctgcag atcatcaact gcctgaccac aatctacgac    9480
aggctggaac aggaacacaa caacctggtc aacgtgcccc tgtgcgtgga catgtgcctg    9540
aattggctgc tgaacgtgta cgacaccggc agaaccggca ggatcagagt gctgtccttt    9600
aagaccggca tcatcagcct gtgcaaggcc cacctggaag ataagtaccg ctatctgttt    9660
aaacaggtgg ccagctctac cggcttctgc gaccagagaa ggctgggact gctgctgcac    9720
gactccatcc agatccccag acagctggga gaggtggcct ccttcggcgg cagcaacatc    9780
gagcctagcg tgcggagctg cttccagttc gccaacaaca gcccgagat cgaagccgcc     9840 ctgttcctgg attggatgag gctggaacct cagtctatgg tctggctgcc cgtgctgcac    9900
agggtggccg ctgccgagac agccaagcac caggccaagt gcaacatctg caaagagtgc    9960
cccatcatcg gcttcagata tcggtccctg aagcacttca actacgatat ctgccagagc    10020
tgcttcttca gcggcagagt ggccaagggc cacaagatgc attacccat ggtgaatac     10080 tgcacccca ccaccagcgg cgaggatgtg cgggacttcg ccaaggtgct gaagaacaaa    10140
ttcaggacta agcgctactt cgctaagcac cctagaatgg gctatctgcc tgtgcagaca    10200
gtgctggaag gcgacaacat ggaaccccc gtgccctga tcaacttttg gccgtggac      10260 agcgcacctg ccagcagtcc tcagctgagc cacgacgaca cccacagcag aatcgagcac    10320
tacgcctcca gactggccga gatggaaaac agcaacggca gctacctgaa cgacagcatc    10380
tcccccaacg agagcatcga cgacgagcat ctgctgatcc agcactactg ccagtccctg    10440
```

-continued

```
aaccaggaca gccccctgag ccagcccaga tcccctgccc agatcctgat ctccctggaa    10500
agcgaggaaa gaggcgagct ggaaaggatc ctggctgacc tggaagagga aaacagaaac    10560
ctgcaggccg agtacgacag actgaagcag cagcacgagc acaagggcct gagccccctg    10620
cctagccccc ctgagatgat gcccaccagc cctcagagcc caggacgc tgagctgatc      10680 gccgaggcca agctgctgag gcagcataag ggccggctgg aagcccggat gcagatcctg    10740
gaagatcaca acaaacagct ggaaagccag ctgcacagac tcagacagct gctgaacag    10800 ccccaggccg aggctaaagt gaacggcacc acagtgtcca gcccctccac ctccctgcag    10860
agatccgaca gcagccagcc catgctgctg agagtggtcg aagccagac cagcgacagc     10920 atgggcgaag aggatctgct gagcccccct caggacacca gcacaggact ggaagaagtg    10980
atggaacagc tgaacaacag cttccccagc agcagaggca gaaacacccc cggcaagccc    11040
atgcgcgagg acaccatgtg a                                              11061
```

<210> SEQ ID NO 2
<211> LENGTH: 3686
<212> TYPE: PRT
<213> ORGANISM: Homo sapiens

<400> SEQUENCE: 2

```
Met Leu Trp Trp Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
```

```
                260                 265                 270
His Tyr Ser Gln Gln Ile Thr Val Ser Leu Ala Gln Gly Tyr Glu Arg
            275                 280                 285
Thr Ser Ser Pro Lys Pro Arg Phe Lys Ser Tyr Ala Tyr Thr Gln Ala
        290                 295                 300
Ala Tyr Val Thr Thr Ser Asp Pro Thr Arg Ser Pro Phe Pro Ser Gln
305                 310                 315                 320
His Leu Glu Ala Pro Glu Asp Lys Ser Phe Gly Ser Ser Leu Met Glu
                325                 330                 335
Ser Glu Val Asn Leu Asp Arg Tyr Gln Thr Ala Leu Glu Glu Val Leu
            340                 345                 350
Ser Trp Leu Leu Ser Ala Glu Asp Thr Leu Gln Ala Gln Gly Glu Ile
        355                 360                 365
Ser Asn Asp Val Glu Val Lys Asp Gln Phe His Thr His Glu Gly
370                 375                 380
Tyr Met Met Asp Leu Thr Ala His Gln Gly Arg Val Gly Asn Ile Leu
385                 390                 395                 400
Gln Leu Gly Ser Lys Leu Ile Gly Thr Gly Lys Leu Ser Glu Asp Glu
            405                 410                 415
Glu Thr Glu Val Gln Glu Gln Met Asn Leu Leu Asn Ser Arg Trp Glu
        420                 425                 430
Cys Leu Arg Val Ala Ser Met Glu Lys Gln Ser Asn Leu His Arg Val
            435                 440                 445
Leu Met Asp Leu Gln Asn Gln Lys Leu Lys Glu Leu Asn Asp Trp Leu
        450                 455                 460
Thr Lys Thr Glu Glu Arg Thr Arg Lys Met Glu Glu Pro Leu Gly
465                 470                 475                 480
Pro Asp Leu Glu Asp Leu Lys Arg Gln Val Gln Gln His Lys Val Leu
                485                 490                 495
Gln Glu Asp Leu Glu Gln Glu Gln Val Arg Val Asn Ser Leu Thr His
            500                 505                 510
Met Val Val Val Asp Glu Ser Ser Gly Asp His Ala Thr Ala Ala
        515                 520                 525
Leu Glu Glu Gln Leu Lys Val Leu Gly Asp Arg Trp Ala Asn Ile Cys
    530                 535                 540
Arg Trp Thr Glu Asp Arg Trp Val Leu Gln Asp Ile Leu Leu Lys
545                 550                 555                 560
Trp Gln Arg Leu Thr Glu Glu Gln Cys Leu Phe Ser Ala Trp Leu Ser
                565                 570                 575
Glu Lys Glu Asp Ala Val Asn Lys Ile His Thr Thr Gly Phe Lys Asp
            580                 585                 590
Gln Asn Glu Met Leu Ser Ser Leu Gln Lys Leu Ala Val Leu Lys Ala
        595                 600                 605
Asp Leu Glu Lys Lys Lys Gln Ser Met Gly Lys Leu Tyr Ser Leu Lys
    610                 615                 620
Gln Asp Leu Leu Ser Thr Leu Lys Asn Lys Ser Val Thr Gln Lys Thr
625                 630                 635                 640
Glu Ala Trp Leu Asp Asn Phe Ala Arg Cys Trp Asp Asn Leu Val Gln
                645                 650                 655
Lys Leu Glu Lys Ser Thr Ala Gln Ile Ser Gln Ala Val Thr Thr Thr
            660                 665                 670
Gln Pro Ser Leu Thr Gln Thr Thr Val Met Glu Thr Val Thr Thr Val
        675                 680                 685
```

```
Thr Thr Arg Glu Gln Ile Leu Val Lys His Ala Gln Glu Glu Leu Pro
690                 695                 700
Pro Pro Pro Gln Lys Lys Arg Gln Ile Thr Val Asp Ser Glu Ile
705                 710                 715                 720
Arg Lys Arg Leu Asp Val Asp Ile Thr Glu Leu His Ser Trp Ile Thr
                725                 730                 735
Arg Ser Glu Ala Val Leu Gln Ser Pro Glu Phe Ala Ile Phe Arg Lys
                740                 745                 750
Glu Gly Asn Phe Ser Asp Leu Lys Glu Lys Val Asn Ala Ile Glu Arg
                755                 760                 765
Glu Lys Ala Glu Lys Phe Arg Lys Leu Gln Asp Ala Ser Arg Ser Ala
770                 775                 780
Gln Ala Leu Val Glu Gln Met Val Asn Glu Gly Val Asn Ala Asp Ser
785                 790                 795                 800
Ile Lys Gln Ala Ser Glu Gln Leu Asn Ser Arg Trp Ile Glu Phe Cys
                805                 810                 815
Gln Leu Leu Ser Glu Arg Leu Asn Trp Leu Glu Tyr Gln Asn Asn Ile
                820                 825                 830
Ile Ala Phe Tyr Asn Gln Leu Gln Gln Leu Glu Gln Met Thr Thr Thr
                835                 840                 845
Ala Glu Asn Trp Leu Lys Ile Gln Pro Thr Thr Pro Ser Glu Pro Thr
850                 855                 860
Ala Ile Lys Ser Gln Leu Lys Ile Cys Lys Asp Glu Val Asn Arg Leu
865                 870                 875                 880
Ser Gly Leu Gln Pro Gln Ile Glu Arg Leu Lys Ile Gln Ser Ile Ala
                885                 890                 895
Leu Lys Glu Lys Gly Gln Gly Pro Met Phe Leu Asp Ala Asp Phe Val
                900                 905                 910
Ala Phe Thr Asn His Phe Lys Gln Val Phe Ser Asp Val Gln Ala Arg
                915                 920                 925
Glu Lys Glu Leu Gln Thr Ile Phe Asp Thr Leu Pro Pro Met Arg Tyr
930                 935                 940
Gln Glu Thr Met Ser Ala Ile Arg Thr Trp Val Gln Gln Ser Glu Thr
945                 950                 955                 960
Lys Leu Ser Ile Pro Gln Leu Ser Val Thr Asp Tyr Glu Ile Met Glu
                965                 970                 975
Gln Arg Leu Gly Glu Leu Gln Ala Leu Gln Ser Ser Leu Gln Glu Gln
                980                 985                 990
Gln Ser Gly Leu Tyr Tyr Leu Ser Thr Thr Val Lys Glu Met Ser Lys
                995                 1000                1005
Lys Ala Pro Ser Glu Ile Ser Arg Lys Tyr Gln Ser Glu Phe Glu
     1010                1015                1020
Glu Ile Glu Gly Arg Trp Lys Lys Leu Ser Ser Gln Leu Val Glu
     1025                1030                1035
His Cys Gln Lys Leu Glu Glu Gln Met Asn Lys Leu Arg Lys Ile
     1040                1045                1050
Gln Asn His Ile Gln Thr Leu Lys Lys Trp Met Ala Glu Val Asp
     1055                1060                1065
Val Phe Leu Lys Glu Glu Trp Pro Ala Leu Gly Asp Ser Glu Ile
     1070                1075                1080
Leu Lys Lys Gln Leu Lys Gln Cys Arg Leu Leu Val Ser Asp Ile
     1085                1090                1095
```

```
Gln Thr Ile Gln Pro Ser Leu Asn Ser Val Asn Glu Gly Gly Gln
1100                1105                1110

Lys Ile Lys Asn Glu Ala Glu Pro Glu Phe Ala Ser Arg Leu Glu
1115                1120                1125

Thr Glu Leu Lys Glu Leu Asn Thr Gln Trp Asp His Met Cys Gln
1130                1135                1140

Gln Val Tyr Ala Arg Lys Glu Ala Leu Lys Gly Gly Leu Glu Lys
1145                1150                1155

Thr Val Ser Leu Gln Lys Asp Leu Ser Glu Met His Glu Trp Met
1160                1165                1170

Thr Gln Ala Glu Glu Tyr Leu Glu Arg Asp Phe Glu Tyr Lys
1175                1180                1185

Thr Pro Asp Glu Leu Gln Lys Ala Val Glu Glu Met Lys Arg Ala
1190                1195                1200

Lys Glu Glu Ala Gln Gln Lys Glu Ala Lys Val Lys Leu Leu Thr
1205                1210                1215

Glu Ser Val Asn Ser Val Ile Ala Gln Ala Pro Pro Val Ala Gln
1220                1225                1230

Glu Ala Leu Lys Lys Glu Leu Glu Thr Leu Thr Thr Asn Tyr Gln
1235                1240                1245

Trp Leu Cys Thr Arg Leu Asn Gly Lys Cys Lys Thr Leu Glu Glu
1250                1255                1260

Val Trp Ala Cys Trp His Glu Leu Leu Ser Tyr Leu Glu Lys Ala
1265                1270                1275

Asn Lys Trp Leu Asn Glu Val Glu Phe Lys Leu Lys Thr Thr Glu
1280                1285                1290

Asn Ile Pro Gly Gly Ala Glu Glu Ile Ser Glu Val Leu Asp Ser
1295                1300                1305

Leu Glu Asn Leu Met Arg His Ser Glu Asp Asn Pro Asn Gln Ile
1310                1315                1320

Arg Ile Leu Ala Gln Thr Leu Thr Asp Gly Gly Val Met Asp Glu
1325                1330                1335

Leu Ile Asn Glu Glu Leu Glu Thr Phe Asn Ser Arg Trp Arg Glu
1340                1345                1350

Leu His Glu Glu Ala Val Arg Arg Gln Lys Leu Leu Glu Gln Ser
1355                1360                1365

Ile Gln Ser Ala Gln Glu Thr Glu Lys Ser Leu His Leu Ile Gln
1370                1375                1380

Glu Ser Leu Thr Phe Ile Asp Lys Gln Leu Ala Ala Tyr Ile Ala
1385                1390                1395

Asp Lys Val Asp Ala Ala Gln Met Pro Gln Glu Ala Gln Lys Ile
1400                1405                1410

Gln Ser Asp Leu Thr Ser His Glu Ile Ser Leu Glu Glu Met Lys
1415                1420                1425

Lys His Asn Gln Gly Lys Glu Ala Ala Gln Arg Val Leu Ser Gln
1430                1435                1440

Ile Asp Val Ala Gln Lys Lys Leu Gln Asp Val Ser Met Lys Phe
1445                1450                1455

Arg Leu Phe Gln Lys Pro Ala Asn Phe Glu Gln Arg Leu Gln Glu
1460                1465                1470

Ser Lys Met Ile Leu Asp Glu Val Lys Met His Leu Pro Ala Leu
1475                1480                1485

Glu Thr Lys Ser Val Glu Gln Glu Val Val Gln Ser Gln Leu Asn
```

-continued

```
                1490                1495                1500
His Cys Val Asn Leu Tyr Lys Ser Leu Ser Glu Val Lys Ser Glu
    1505                1510                1515
Val Glu Met Val Ile Lys Thr Gly Arg Gln Ile Val Gln Lys Lys
    1520                1525                1530
Gln Thr Glu Asn Pro Lys Glu Leu Asp Glu Arg Val Thr Ala Leu
    1535                1540                1545
Lys Leu His Tyr Asn Glu Leu Gly Ala Lys Val Thr Glu Arg Lys
    1550                1555                1560
Gln Gln Leu Glu Lys Cys Leu Lys Leu Ser Arg Lys Met Arg Lys
    1565                1570                1575
Glu Met Asn Val Leu Thr Glu Trp Leu Ala Ala Thr Asp Met Glu
    1580                1585                1590
Leu Thr Lys Arg Ser Ala Val Glu Gly Met Pro Ser Asn Leu Asp
    1595                1600                1605
Ser Glu Val Ala Trp Gly Lys Ala Thr Gln Lys Glu Ile Glu Lys
    1610                1615                1620
Gln Lys Val His Leu Lys Ser Ile Thr Glu Val Gly Glu Ala Leu
    1625                1630                1635
Lys Thr Val Leu Gly Lys Lys Glu Thr Leu Val Glu Asp Lys Leu
    1640                1645                1650
Ser Leu Leu Asn Ser Asn Trp Ile Ala Val Thr Ser Arg Ala Glu
    1655                1660                1665
Glu Trp Leu Asn Leu Leu Leu Glu Tyr Gln Lys His Met Glu Thr
    1670                1675                1680
Phe Asp Gln Asn Val Asp His Ile Thr Lys Trp Ile Ile Gln Ala
    1685                1690                1695
Asp Thr Leu Leu Asp Glu Ser Glu Lys Lys Lys Pro Gln Gln Lys
    1700                1705                1710
Glu Asp Val Leu Lys Arg Leu Lys Ala Glu Leu Asn Asp Ile Arg
    1715                1720                1725
Pro Lys Val Asp Ser Thr Arg Asp Gln Ala Ala Asn Leu Met Ala
    1730                1735                1740
Asn His Gly Asp His Cys Arg Lys Leu Val Glu Pro Gln Ile Ser
    1745                1750                1755
Glu Leu Asn His Arg Phe Ala Ala Ile Ser His Arg Ile Lys Thr
    1760                1765                1770
Gly Lys Ala Ser Ile Pro Leu Lys Glu Leu Glu Gln Phe Asn Ser
    1775                1780                1785
Asp Ile Gln Lys Leu Leu Glu Pro Leu Glu Ala Glu Ile Gln Gln
    1790                1795                1800
Gly Val Asn Leu Lys Glu Glu Asp Phe Asn Lys Asp Met Asn Glu
    1805                1810                1815
Asp Asn Glu Gly Thr Val Lys Glu Leu Leu Gln Arg Gly Asp Asn
    1820                1825                1830
Leu Gln Gln Arg Ile Thr Asp Glu Arg Lys Arg Glu Glu Ile Lys
    1835                1840                1845
Ile Lys Gln Gln Leu Leu Gln Thr Lys His Asn Ala Leu Lys Asp
    1850                1855                1860
Leu Arg Ser Gln Arg Arg Lys Lys Ala Leu Glu Ile Ser His Gln
    1865                1870                1875
Trp Tyr Gln Tyr Lys Arg Gln Ala Asp Asp Leu Leu Lys Cys Leu
    1880                1885                1890
```

-continued

```
Asp Asp Ile Glu Lys Lys Leu Ala Ser Leu Pro Glu Pro Arg Asp
    1895              1900                1905

Glu Arg Lys Ile Lys Glu Ile Asp Arg Glu Leu Gln Lys Lys Lys
    1910              1915                1920

Glu Glu Leu Asn Ala Val Arg Arg Gln Ala Glu Gly Leu Ser Glu
    1925              1930                1935

Asp Gly Ala Ala Met Ala Val Glu Pro Thr Gln Ile Gln Leu Ser
    1940              1945                1950

Lys Arg Trp Arg Glu Ile Glu Ser Lys Phe Ala Gln Phe Arg Arg
    1955              1960                1965

Leu Asn Phe Ala Gln Ile His Thr Val Arg Glu Glu Thr Met Met
    1970              1975                1980

Val Met Thr Glu Asp Met Pro Leu Glu Ile Ser Tyr Val Pro Ser
    1985              1990                1995

Thr Tyr Leu Thr Glu Ile Thr His Val Ser Gln Ala Leu Leu Glu
    2000              2005                2010

Val Glu Gln Leu Leu Asn Ala Pro Asp Leu Cys Ala Lys Asp Phe
    2015              2020                2025

Glu Asp Leu Phe Lys Gln Glu Glu Ser Leu Lys Asn Ile Lys Asp
    2030              2035                2040

Ser Leu Gln Gln Ser Ser Gly Arg Ile Asp Ile Ile His Ser Lys
    2045              2050                2055

Lys Thr Ala Ala Leu Gln Ser Ala Thr Pro Val Glu Arg Val Lys
    2060              2065                2070

Leu Gln Glu Ala Leu Ser Gln Leu Asp Phe Gln Trp Glu Lys Val
    2075              2080                2085

Asn Lys Met Tyr Lys Asp Arg Gln Gly Arg Phe Asp Arg Ser Val
    2090              2095                2100

Glu Lys Trp Arg Arg Phe His Tyr Asp Ile Lys Ile Phe Asn Gln
    2105              2110                2115

Trp Leu Thr Glu Ala Glu Gln Phe Leu Arg Lys Thr Gln Ile Pro
    2120              2125                2130

Glu Asn Trp Glu His Ala Lys Tyr Lys Trp Tyr Leu Lys Glu Leu
    2135              2140                2145

Gln Asp Gly Ile Gly Gln Arg Gln Thr Val Val Arg Thr Leu Asn
    2150              2155                2160

Ala Thr Gly Glu Glu Ile Ile Gln Gln Ser Ser Lys Thr Asp Ala
    2165              2170                2175

Ser Ile Leu Gln Glu Lys Leu Gly Ser Leu Asn Leu Arg Trp Gln
    2180              2185                2190

Glu Val Cys Lys Gln Leu Ser Asp Arg Lys Lys Arg Leu Glu Glu
    2195              2200                2205

Gln Lys Asn Ile Leu Ser Glu Phe Gln Arg Asp Leu Asn Glu Phe
    2210              2215                2220

Val Leu Trp Leu Glu Glu Ala Asp Asn Ile Ala Ser Ile Pro Leu
    2225              2230                2235

Glu Pro Gly Lys Glu Gln Gln Leu Lys Glu Lys Leu Glu Gln Val
    2240              2245                2250

Lys Leu Leu Val Glu Glu Leu Pro Leu Arg Gln Gly Arg Ile Leu
    2255              2260                2265

Lys Gln Leu Asn Glu Thr Gly Gly Pro Val Leu Val Ser Ala Pro
    2270              2275                2280
```

-continued

| | | | | | | | | | | | |
|---|---|---|---|---|---|---|---|---|---|---|---|
| Ile | Ser | Pro | Glu | Glu | Gln | Asp | Lys | Leu | Glu | Asn | Lys | Leu | Lys | Gln |
| | 2285 | | | | 2290 | | | | 2295 | | |

Ile Ser Pro Glu Glu Gln Asp Lys Leu Glu Asn Lys Leu Lys Gln
2285                2290                2295

Thr Asn Leu Gln Trp Ile Lys Val Ser Arg Ala Leu Pro Glu Lys
2300                2305                2310

Gln Gly Glu Ile Glu Ala Gln Ile Lys Asp Leu Gly Gln Leu Glu
2315                2320                2325

Lys Lys Leu Glu Asp Leu Glu Glu Gln Leu Asn His Leu Leu Leu
2330                2335                2340

Trp Leu Ser Pro Ile Arg Asn Gln Leu Glu Ile Tyr Asn Gln Pro
2345                2350                2355

Asn Gln Glu Gly Pro Phe Asp Val Lys Glu Thr Glu Ile Ala Val
2360                2365                2370

Gln Ala Lys Gln Pro Asp Val Glu Glu Ile Leu Ser Lys Gly Gln
2375                2380                2385

His Leu Tyr Lys Glu Lys Pro Ala Thr Gln Pro Val Lys Arg Lys
2390                2395                2400

Leu Glu Asp Leu Ser Ser Glu Trp Lys Ala Val Asn Arg Leu Leu
2405                2410                2415

Gln Glu Leu Arg Ala Lys Gln Pro Asp Leu Ala Pro Gly Leu Thr
2420                2425                2430

Thr Ile Gly Ala Ser Pro Thr Gln Thr Val Thr Leu Val Thr Gln
2435                2440                2445

Pro Val Val Thr Lys Glu Thr Ala Ile Ser Lys Leu Glu Met Pro
2450                2455                2460

Ser Ser Leu Met Leu Glu Val Pro Ala Leu Ala Asp Phe Asn Arg
2465                2470                2475

Ala Trp Thr Glu Leu Thr Asp Trp Leu Ser Leu Leu Asp Gln Val
2480                2485                2490

Ile Lys Ser Gln Arg Val Met Val Gly Asp Leu Glu Asp Ile Asn
2495                2500                2505

Glu Met Ile Ile Lys Gln Lys Ala Thr Met Gln Asp Leu Glu Gln
2510                2515                2520

Arg Arg Pro Gln Leu Glu Glu Leu Ile Thr Ala Ala Gln Asn Leu
2525                2530                2535

Lys Asn Lys Thr Ser Asn Gln Glu Ala Arg Thr Ile Ile Thr Asp
2540                2545                2550

Arg Ile Glu Arg Ile Gln Asn Gln Trp Asp Glu Val Gln Glu His
2555                2560                2565

Leu Gln Asn Arg Arg Gln Gln Leu Asn Glu Met Leu Lys Asp Ser
2570                2575                2580

Thr Gln Trp Leu Glu Ala Lys Glu Glu Ala Glu Gln Val Leu Gly
2585                2590                2595

Gln Ala Arg Ala Lys Leu Glu Ser Trp Lys Glu Gly Pro Tyr Thr
2600                2605                2610

Val Asp Ala Ile Gln Lys Lys Ile Thr Glu Thr Lys Gln Leu Ala
2615                2620                2625

Lys Asp Leu Arg Gln Trp Gln Thr Asn Val Asp Val Ala Asn Asp
2630                2635                2640

Leu Ala Leu Lys Leu Leu Arg Asp Tyr Ser Ala Asp Asp Thr Arg
2645                2650                2655

Lys Val His Met Ile Thr Glu Asn Ile Asn Ala Ser Trp Arg Ser
2660                2665                2670

Ile His Lys Arg Val Ser Glu Arg Glu Ala Ala Leu Glu Glu Thr

```
                2675                2680                2685

His Arg Leu Leu Gln Gln Phe Pro Leu Asp Leu Glu Lys Phe Leu
    2690                2695                2700

Ala Trp Leu Thr Glu Ala Glu Thr Thr Ala Asn Val Leu Gln Asp
    2705                2710                2715

Ala Thr Arg Lys Glu Arg Leu Leu Glu Asp Ser Lys Gly Val Lys
    2720                2725                2730

Glu Leu Met Lys Gln Trp Gln Asp Leu Gln Gly Glu Ile Glu Ala
    2735                2740                2745

His Thr Asp Val Tyr His Asn Leu Asp Glu Asn Ser Gln Lys Ile
    2750                2755                2760

Leu Arg Ser Leu Glu Gly Ser Asp Asp Ala Val Leu Leu Gln Arg
    2765                2770                2775

Arg Leu Asp Asn Met Asn Phe Lys Trp Ser Glu Leu Arg Lys Lys
    2780                2785                2790

Ser Leu Asn Ile Arg Ser His Leu Glu Ala Ser Ser Asp Gln Trp
    2795                2800                2805

Lys Arg Leu His Leu Ser Leu Gln Glu Leu Leu Val Trp Leu Gln
    2810                2815                2820

Leu Lys Asp Asp Glu Leu Ser Arg Gln Ala Pro Ile Gly Gly Asp
    2825                2830                2835

Phe Pro Ala Val Gln Lys Gln Asn Asp Val His Arg Ala Phe Lys
    2840                2845                2850

Arg Glu Leu Lys Thr Lys Glu Pro Val Ile Met Ser Thr Leu Glu
    2855                2860                2865

Thr Val Arg Ile Phe Leu Thr Glu Gln Pro Leu Glu Gly Leu Glu
    2870                2875                2880

Lys Leu Tyr Gln Glu Pro Arg Glu Leu Pro Pro Glu Glu Arg Ala
    2885                2890                2895

Gln Asn Val Thr Arg Leu Leu Arg Lys Gln Ala Glu Glu Val Asn
    2900                2905                2910

Thr Glu Trp Glu Lys Leu Asn Leu His Ser Ala Asp Trp Gln Arg
    2915                2920                2925

Lys Ile Asp Glu Thr Leu Glu Arg Leu Gln Glu Leu Gln Glu Ala
    2930                2935                2940

Thr Asp Glu Leu Asp Leu Lys Leu Arg Gln Ala Glu Val Ile Lys
    2945                2950                2955

Gly Ser Trp Gln Pro Val Gly Asp Leu Leu Ile Asp Ser Leu Gln
    2960                2965                2970

Asp His Leu Glu Lys Val Lys Ala Leu Arg Gly Glu Ile Ala Pro
    2975                2980                2985

Leu Lys Glu Asn Val Ser His Val Asn Asp Leu Ala Arg Gln Leu
    2990                2995                3000

Thr Thr Leu Gly Ile Gln Leu Ser Pro Tyr Asn Leu Ser Thr Leu
    3005                3010                3015

Glu Asp Leu Asn Thr Arg Trp Lys Leu Leu Gln Val Ala Val Glu
    3020                3025                3030

Asp Arg Val Arg Gln Leu His Glu Ala His Arg Asp Phe Gly Pro
    3035                3040                3045

Ala Ser Gln His Phe Leu Ser Thr Ser Val Gln Gly Pro Trp Glu
    3050                3055                3060

Arg Ala Ile Ser Pro Asn Lys Val Pro Tyr Tyr Ile Asn His Glu
    3065                3070                3075
```

-continued

Thr Gln Thr Thr Cys Trp Asp His Pro Lys Met Thr Glu Leu Tyr
    3080          3085             3090

Gln Ser Leu Ala Asp Leu Asn Asn Val Arg Phe Ser Ala Tyr Arg
    3095          3100             3105

Thr Ala Met Lys Leu Arg Arg Leu Gln Lys Ala Leu Cys Leu Asp
    3110          3115             3120

Leu Leu Ser Leu Ser Ala Ala Cys Asp Ala Leu Asp Gln His Asn
    3125          3130             3135

Leu Lys Gln Asn Asp Gln Pro Met Asp Ile Leu Gln Ile Ile Asn
    3140          3145             3150

Cys Leu Thr Thr Ile Tyr Asp Arg Leu Glu Gln Glu His Asn Asn
    3155          3160             3165

Leu Val Asn Val Pro Leu Cys Val Asp Met Cys Leu Asn Trp Leu
    3170          3175             3180

Leu Asn Val Tyr Asp Thr Gly Arg Thr Gly Arg Ile Arg Val Leu
    3185          3190             3195

Ser Phe Lys Thr Gly Ile Ile Ser Leu Cys Lys Ala His Leu Glu
    3200          3205             3210

Asp Lys Tyr Arg Tyr Leu Phe Lys Gln Val Ala Ser Ser Thr Gly
    3215          3220             3225

Phe Cys Asp Gln Arg Arg Leu Gly Leu Leu Leu His Asp Ser Ile
    3230          3235             3240

Gln Ile Pro Arg Gln Leu Gly Glu Val Ala Ser Phe Gly Gly Ser
    3245          3250             3255

Asn Ile Glu Pro Ser Val Arg Ser Cys Phe Gln Phe Ala Asn Asn
    3260          3265             3270

Lys Pro Glu Ile Glu Ala Ala Leu Phe Leu Asp Trp Met Arg Leu
    3275          3280             3285

Glu Pro Gln Ser Met Val Trp Leu Pro Val Leu His Arg Val Ala
    3290          3295             3300

Ala Ala Glu Thr Ala Lys His Gln Ala Lys Cys Asn Ile Cys Lys
    3305          3310             3315

Glu Cys Pro Ile Ile Gly Phe Arg Tyr Arg Ser Leu Lys His Phe
    3320          3325             3330

Asn Tyr Asp Ile Cys Gln Ser Cys Phe Phe Ser Gly Arg Val Ala
    3335          3340             3345

Lys Gly His Lys Met His Tyr Pro Met Val Glu Tyr Cys Thr Pro
    3350          3355             3360

Thr Thr Ser Gly Glu Asp Val Arg Asp Phe Ala Lys Val Leu Lys
    3365          3370             3375

Asn Lys Phe Arg Thr Lys Arg Tyr Phe Ala Lys His Pro Arg Met
    3380          3385             3390

Gly Tyr Leu Pro Val Gln Thr Val Leu Glu Gly Asp Asn Met Glu
    3395          3400             3405

Thr Pro Val Thr Leu Ile Asn Phe Trp Pro Val Asp Ser Ala Pro
    3410          3415             3420

Ala Ser Ser Pro Gln Leu Ser His Asp Asp Thr His Ser Arg Ile
    3425          3430             3435

Glu His Tyr Ala Ser Arg Leu Ala Glu Met Glu Asn Ser Asn Gly
    3440          3445             3450

Ser Tyr Leu Asn Asp Ser Ile Ser Pro Asn Glu Ser Ile Asp Asp
    3455          3460             3465

| | | | | | | | | | |
|---|---|---|---|---|---|---|---|---|---|
| Glu | His | Leu | Leu | Ile | Gln | His | Tyr | Cys | Gln | Ser | Leu | Asn | Gln | Asp |
| | 3470 | | | | 3475 | | | | 3480 | | |

Ser Pro Leu Ser Gln Pro Arg Ser Pro Ala Gln Ile Leu Ile Ser
    3485            3490            3495

Leu Glu Ser Glu Glu Arg Gly Glu Leu Glu Arg Ile Leu Ala Asp
    3500            3505            3510

Leu Glu Glu Glu Asn Arg Asn Leu Gln Ala Glu Tyr Asp Arg Leu
    3515            3520            3525

Lys Gln Gln His Glu His Lys Gly Leu Ser Pro Leu Pro Ser Pro
    3530            3535            3540

Pro Glu Met Met Pro Thr Ser Pro Gln Ser Pro Arg Asp Ala Glu
    3545            3550            3555

Leu Ile Ala Glu Ala Lys Leu Leu Arg Gln His Lys Gly Arg Leu
    3560            3565            3570

Glu Ala Arg Met Gln Ile Leu Glu Asp His Asn Lys Gln Leu Glu
    3575            3580            3585

Ser Gln Leu His Arg Leu Arg Gln Leu Leu Glu Gln Pro Gln Ala
    3590            3595            3600

Glu Ala Lys Val Asn Gly Thr Thr Val Ser Ser Pro Ser Thr Ser
    3605            3610            3615

Leu Gln Arg Ser Asp Ser Ser Gln Pro Met Leu Leu Arg Val Val
    3620            3625            3630

Gly Ser Gln Thr Ser Asp Ser Met Gly Glu Glu Asp Leu Leu Ser
    3635            3640            3645

Pro Pro Gln Asp Thr Ser Thr Gly Leu Glu Glu Val Met Glu Gln
    3650            3655            3660

Leu Asn Asn Ser Phe Pro Ser Ser Arg Gly Arg Asn Thr Pro Gly
    3665            3670            3675

Lys Pro Met Arg Glu Asp Thr Met
    3680            3685

<210> SEQ ID NO 3
<211> LENGTH: 11067
<212> TYPE: DNA
<213> ORGANISM: Artificial sequence
<220> FEATURE:
<223> OTHER INFORMATION: Codon optimised dystrophin cDNA including Kozak
      sequence

<400> SEQUENCE: 3
gccaccatgc tgtggtggga ggaagtggaa gattgctacg agcgcgagga cgtgcagaag      60
aaaaccttca ccaaatgggt caacgcccag ttcagcaagt tcggcaagca gcacatcgag     120
aacctgttca gcgacctgca ggacggcaga aggctgctgg acctgctgga aggcctgacc     180
ggccagaagc tgcccaaaga aagggcagc accagagtgc acgccctgaa caacgtgaac     240
aaggccctga gtgctgca gaacaacaac gtggacctgg tcaacatcgg cagcaccgac     300
atcgtggacg gcaaccacaa gctgaccctg ggcctgatct ggaacatcat cctgcactgg     360
caggtcaaaa acgtgatgaa gaacatcatg gccggcctgc agcagaccaa cagcgagaag     420
atcctgctga gctgggtccg ccagagcacc agaaactacc cccaggtcaa cgtgatcaac     480
ttcaccacct cttggagcga cggcctggcc ctgaacgccc tgatccacag ccacagaccc     540
gacctgttcg actggaacag cgtggtctgc cagcagagcg ccaccccagag actggaacac     600 gccttcaata tcgccagata ccagctgggc atcgagaagc tgctggatcc cgaggacgtg     660
gacaccacct accccgacaa gaaatccatc ctgatgtaca tcaccagcct gttccaggtg     720

-continued

```
ctgccccagc aggtctccat cgaggccatc aggaagtgg aaatgctgcc cagacccccc        780
aaagtgacca agaggaaca cttccagctg caccaccaga tgcactacag ccagcagatc        840
accgtgtccc tggctcaggg ctacgagaga accagcagcc ccaagcccag attcaagagc       900
tacgcctaca cccaggccgc ctacgtgacc accagcgacc ccaccagaag cccattcccc       960
agccagcacc tggaagcccc cgaggacaag agcttcggca gcagcctgat ggaaagcgaa      1020
gtgaacctgg acagatacca gaccgccctg aagaggtgc tgtcctggct gctgtccgcc       1080
gaggacacac tgcaggccca gggcgagatc agcaacgacg tggaagtggt caaagaccag      1140
ttccacaccc acgagggcta catgatggac ctgaccgccc accagggcag agtgggcaac      1200
atcctgcagc tgggcagcaa gctgatcggc accggcaagc tgagcgagga cgaagagaca      1260
gaggtgcagg aacagatgaa cctgctgaac agcagatggg agtgcctgag agtggccagc      1320
atggaaaagc agagcaacct gcacagagtg ctgatggatc tgcagaacca gaagctgaaa      1380
gagctgaacg actggctgac caagaccgag gaacggacca gaaagatgga agaggaaccc      1440
ctgggccccg acctggaaga tctgaagaga caggtgcagc agcacaaggt gctgcaggaa      1500
gatctggaac aggaacaggt ccgcgtcaac agcctgaccc acatggtggt ggtggtggac      1560
gagagcagcg gcgatcacgc caccgccgct ctggaagaac agctgaaggt gctgggcgac      1620
agatgggcca acatctgccg gtggaccgag gacagatggg tgctgctgca ggacatcctg      1680
ctgaagtggc agagactgac agaggaacag tgcctgttct ccgcctggct gagcgagaaa      1740
gaggacgccg tcaacaagat ccacaccacc ggcttcaagg accagaacga gatgctgagc      1800
agcctgcaga actggccgt gctgaaggcc gatctggaaa agaaaaagca gtccatgggc      1860
aagctgtaca gcctgaagca ggacctgctg tccaccctga gaacaagag cgtgacccag      1920
aaaaccgagg cctggctgga caacttcgcc agatgctggg acaacctggt gcagaagctg      1980
gaaaagagca ccgcccagat cagccaggcc gtgaccacaa cccagccctc cctgacccag      2040
accaccgtga tggaaaccgt gaccactgtg accacccgcg agcagatcct ggtcaaacac      2100
gcccaggaag aactgccccc tccaccccc cagaagaaaa gacagatcac agtggacagc      2160
gagatcagaa agcggctgga tgtggacatc accgagctgc acagctggat caccagatcc      2220
gaggccgtgc tgcagagccc cgagttcgcc atcttcagaa agagggcaa cttctccgac      2280
ctgaaagaaa agtgaacgc catcgagaga gagaaggccg agaagttcag aaagctgcag      2340
gacgccagcc gctctgctca ggctctggtg aacagatgg tcaacgaggg cgtgaacgcc      2400
gacagcatca gcaggccag cgagcagctg aactccagat ggatcgagtt ctgccagctg      2460
ctgtccgaga gactgaactg gctggaatac cagaacaaca tcattgcctt ctacaaccag      2520
ctccagcagc tggaacagat gaccaccacc gccgagaact ggctgaagat ccagcccacc      2580
accccagcg agcccaccgc catcaagagc cagctgaaga tctgcaagga cgaagtgaac      2640
agactgtctg gcctgcagcc ccagatcgag aggctgaaga ttcagtctat cgccctgaaa      2700
gagaaaggcc agggccccat gttcctggac gccgacttcg tggccttcac caaccacttc      2760
aaacaggtgt tctccgacgt gcaggccaga gagaaagagc tgcagaccat cttcgacacc      2820
ctgccccca tgagatacca ggaaaccatg agcgccatca gaacctgggt gcagcagagc      2880
gagacaaagc tgagcatccc ccagctgagc gtgaccgact acgagatcat ggaacagaga      2940
ctgggcgagc tgcaggctct gcagtccagt ctgcaggaac agcagagcgg cctgtactac      3000
ctgagcacca ccgtgaaaga gatgagcaag aaggccccct ccgagatctc cagaaagtac      3060
```

```
cagagcgagt tcgaagagat cgagggcaga tggaagaagc tgtcctctca gctggtggaa      3120
cactgccaga aactggaaga acagatgaac aagctgcgga agatccagaa ccacatccag      3180
accctgaaaa agtggatggc cgaggtggac gtgttcctga agaggaatg gcctgccctg       3240 ggcgactccg agatcctgaa aaagcagctg aagcagtgca gactgctggt gtccgacatc      3300
cagacaatcc agcccagcct gaactccgtg aatgagggcg ccagaagat caagaacgag       3360 gccgagcctg agttcgccag cagactggaa accgagctga agaactgaa tacccagtgg       3420 gaccacatgt gtcagcaggt ctacgcccgg aaagaggccc tgaagggcgg cctggaaaag     3480
accgtgtctc tgcagaaaga cctgtccgag atgcacgagt ggatgaccca ggccgaggaa     3540
gagtacctgg aaagagactt cgagtacaag accccgacg agctgcagaa agctgtggaa     3600
gaaatgaaga gggccaaaga agaggcccag cagaaagagg ccaaagtcaa gctgctgacc     3660
gagtccgtga acagcgtgat cgcccaggcc cctcccgtgg ctcaggaagc cctgaagaaa     3720
gaactggaaa cactgaccac caactaccag tggctgtgca ccagactgaa cggcaagtgc     3780
aagaccctgg aagaagtgtg ggcctgctgg cacgagctgc tgagctacct ggaaaaggcc     3840
aacaagtggc tgaacgaggt ggaattcaag ctgaaaacca ccgagaacat ccctggcggc     3900
gctgaagaga tcagcgaggt gctggacagc ctggaaaacc tgatgagaca cagcgaggac     3960
aaccccaacc agatcagaat cctggcccag acactgaccg acggcggcgt gatggacgag     4020
ctgatcaacg aggaactgga aaccttcaac agccggtggc gcgagctgca cgaggaagct     4080
gtgcggagac agaaactgct ggaacagtcc atccagagcg cccaggaaac cgagaagtcc     4140
ctgcacctga tccaggaaag cctgacattc atcgacaagc agctggccgc ctatatcgcc     4200
gacaaggtgg acgccgccca gatgccacag gaagctcaga agatccagtc cgacctgacc     4260
agccacgaga tcagcctgga agagatgaag aagcacaacc agggcaaaga ggccgcccag     4320
agggtcctga gccagatcga cgtggcccag aaaaaactgc aggacgtgtc catgaagttc     4380
aggctgttcc agaagcccgc caacttcgag cagagactgc aggaatccaa gatgatcctg     4440
gatgaagtga agatgcatct gccagccctg gaaacaaagt ccgtggaaca ggaagtggtc     4500
cagtcccagc tgaaccactg cgtgaacctg tacaagagcc tgtccgaagt gaagtccgag     4560
gtggaaatgg tcatcaagac cggcagacag atcgtgcaga aaaagcagac cgagaacccc     4620
aaagaactgg acgagagagt gaccgccctg aagctgcact acaacgagct gggcgccaaa     4680
gtgacagagc ggaaacagca gctggaaaag tgcctgaagc tgtcccgcaa gatgcggaaa     4740
gaaatgaacg tgctgacaga gtggctggct gccaccgaca tggaactgac caagagaagc     4800
gccgtggaag gcatgccag caacctggac tccgaggtgg catggggcaa ggccacccag     4860
aaagagatcg aaaagcagaa ggtgcacctg aagtccatca ccgaagtggg cgaggctctg     4920
aaaaccgtgc tgggcaagaa agaaaccctg gtggaagata gctgagcct gctgaactct      4980 aactggatcg ccgtgaccag cagagccgag gaatggctga atctgctgct ggaatatcag    5040
aaacacatgg aaacctttga ccagaacgtg gaccacatca ccaagtggat catccaggct    5100
gacaccctgc tggacgagtc cgagaagaag aaacctcagc agaaagaaga tgtgctgaag    5160
agactgaagc tgagctgaa tgacatcaga cccaaggtgg acagcaccag gaccaggcc     5220 gccaacctga tggccaacca cggcgaccac tgcagaaaac tggtggaacc ccagatctcc    5280
gagctgaatc acagattcgc cgccatcagc cacagaatca agacaggcaa ggccagcatc    5340
cccctgaaag agctggaaca gttcaacagc gacatccaga agctgctgga accccctggaa   5400 gccgagatcc agcagggcgt gaacctgaaa gaagaggact tcaacaagga catgaacgag    5460
```

```
gacaacgagg gcacagtgaa agagctgctc cagagaggcg acaacctgca gcagcgcatc    5520
accgacgaga gaaagcgcga ggaaatcaag atcaagcagc agctcctgca gaccaagcac    5580
aacgccctga aggacctgag atcccagaga agaaagaagg ccctggaaat cagccaccag    5640
tggtatcagt acaagagaca ggccgacgac ctgctgaaat gcctgacgga catcgagaag    5700
aagctggcta gcctgcccga gcccagggac gagaggaaga tcaaagaaat cgaccgggaa    5760
ctgcagaaga gaaagaggga actgaacgcc gtccgcaggc aggccgaggg cctgtctgaa    5820
gatggcgccg ctatggccgt ggaacccacc cagatccagc tgagcaagag atggcgcgag    5880
atcgagagca agttcgccca gttccgcaga ctgaacttcg cccagatcca taccgtgcgg    5940
gaagagacaa tgatggtcat gacagaggac atgcccctgg aaattagcta cgtgcccagc    6000
acctacctga ccgagatcac acacgtgtcc caggcactgc tggaagtgga acagctgctg    6060
aatgcccccg acctgtgcgc caaggacttc gaggatctgt tcaagcagga agagagcctg    6120
aagaatatca aggactccct gcagcagtcc agcggcagaa tcgacatcat ccacagcaag    6180
aaaacagccg ccctgcagag cgctaccccc gtggaacgcg tgaagctgca ggaagcactg    6240
agccagctgg acttccagtg ggagaaagtg aacaaaatgt acaaggaccg gcagggcaga    6300
ttcgacagat ccgtggaaaa gtggcggaga ttccactacg acatcaagat cttcaatcag    6360
tggctgacag aggccgagca gttcctgaga aagacccaga tccctgagaa ctgggagcac    6420
gccaagtaca agtggtatct gaaagaactg caggatggca tcggccagag acagaccgtg    6480
gtccgcacac tgaacgccac cggcgaagag atcatccagc agagcagcaa gaccgacgcc    6540
agcatcctgc aggaaaagct gggctccctg aacctgagat ggcaggaagt gtgcaagcag    6600
ctgagcgaca gaaagaaaag gctggaagaa cagaagaata tcctgagcga gttccagagg    6660
gacctgaacg agttcgtgct gtggctggaa gaggctgaca atatcgcctc catcccctg    6720 gaacccggca agagcagca gctgaaagaa aaactggaac aggtcaaact gctggtggaa    6780
gaactgcctc tgagacaggg cagaatcctg aagcagctga cgagacagg cggccctgtg    6840 ctggtgtctg cccccatcag ccccgaggaa caggacaaac tggaaaacaa actgaagcag    6900
acaaacctgc agtggatcaa ggtgtccaga gccctgcccg agaagcaggg ggagatcgag    6960
gcccagatca aggacctggg ccagctgaaa aaaagctgg aagatctgga agaacagctc    7020
aaccatctgc tgctgtggct gagccccatc agaaaccagc tggaaatcta caatcagccc    7080
aaccaggaag gccccttcga cgtcaaagaa accgagatcg ccgtgcaggc taagcagcct    7140
gacgtggaag agatcctgag caagggacag cacctgtaca agagaagcc tgccacccag    7200 cccgtgaagc gcaaactgga agatctgtcc agcgagtgga aggccgtgaa ccgcctgctg    7260
caggaactga gagccaagca gcccgacctg gcccctggcc tgacaacaat cggcgccagc    7320
cccacccaga cagtgacccc ggtcacacag cccgtggtca caaagagac agccatcagc    7380 aagctggaaa tgcccagctc cctgatgctg gaagtgcccg ccctggccga cttcaacaga    7440
gcctggaccg agctgaccga ttggctgtct ctgctggacc aggtcatcaa gtcccagcgc    7500
gtgatggtcg gcgatctgga agatatcaac gagatgatca tcaagcagaa agccaccatg    7560
caggacctgg aacagaggcg gcctcagctg gaagaactga tcacagccgc ccagaacctg    7620
aaaaacaaga ccagcaacca ggaagccagg accatcatca ccgacagaat cgagaggatc    7680
cagaatcagt gggacgaagt gcaggaacat ctgcagaaca gacgccagca gctgaatgag    7740
atgctgaagg acagcaccca gtggctggaa gctaagaag aggctgaaca ggtcctggga    7800
```

-continued

```
caggccagag ccaagctgga atcttggaaa gagggcccct acaccgtcga cgctatccag   7860
aagaagatca ccgagacaaa acagctggcc aaggacctgc ggcagtggca gaccaacgtg   7920
gacgtggcca acgacctggc tctgaagctg ctgcgggact acagcgccga cgacaccaga   7980
aaggtgcaca tgatcacaga gaacatcaac gcaagttggc ggagcatcca caagagagtg   8040
tctgagcgcg aggctgcact ggaagagact cacagactcc tgcagcagtt ccccctggac   8100
ctggaaaaat tcctggcttg gctgaccgag gctgagacaa ccgccaacgt gctgcaggat   8160
gccaccagaa aagagagact gctggaagat agcaagggcg tgaaagaact gatgaagcag   8220
tggcaggacc tgcagggcga aatcgaggct cacaccgacg tgtaccacaa cctggacgag   8280
aacagccaga agattctgag aagcctggaa ggcagcgacg acgccgtgct gctgcagcgg   8340
agactggaca acatgaactt caagtggtcc gagctgcgca agaagtctct gaacatcaga   8400
tcccatctgg aagccagcag cgaccagtgg aagagactgc acctgagtct gcaggaactg   8460
ctggtctggc tgcagctgaa ggacgacgag ctgagcagac aggcccccat cggcggcgat   8520
ttccccgccg tgcagaaaca gaacgacgtg cacagagcct tcaagagaga gctgaaaaca   8580
aaagaacccg tgatcatgag caccctggaa actgtgcgga tcttcctgac cgagcagccc   8640
ctggaaggac tggaaaagct gtaccaggaa cccagagagc tgccccctga ggaacgggcc   8700
cagaacgtga cccggctgct gagaaagcag gccgaagagg tcaacaccga gtgggagaag   8760
ctgaacctgc actccgccga ctggcagaga agatcgacg agacactgga acgcctgcag   8820
gaactgcagg aagctaccga cgagctggat ctgaaactgc ggcaggctga agtgatcaag   8880
ggcagctggc agcccgtggg ggacctgctg atcgactctc tgcaggacca tctggaaaaa   8940
gtgaaggccc tgaggggcga gatcgctcct ctgaaagaaa acgtgtccca cgtgaacgac   9000
ctggccaggc agctgaccac cctgggcatc cagctgtccc cctacaacct gagcactctg   9060
gaagatctga acaccagatg gaagctgctg caggtcgccg tggaagatag agtgcggcag   9120
ctgcacgaag cccacagaga cttcggcccc gcctcccagc acttcctgtc cacaagcgtg   9180
cagggcccct gggagagggc catcagccct aacaaggtgc cctactacat caaccacgag   9240
acacagacca cctgttggga ccaccccaag atgaccgagc tgtatcagtc tctggccgac   9300
ctgaacaatg tgcggttcag cgcctacaga accgctatga agctgaggcg cctgcagaaa   9360
gccctgtgcc tggacctgct gagcctgagc gccgcctgtg acgccctgga ccagcacaac   9420
ctgaaacaga atgaccagcc catggatatc ctgcagatca tcaactgcct gaccacaatc   9480
tacgacaggt tggaacagga acacaacaac ctggtcaacg tgccgctgtg cgtggacatg   9540
tgcctgaatt ggctgctgaa cgtgtacgac accggcagaa ccggcaggat cagagtgctg   9600
tcctttaaga ccggcatcat cagcctgtgc aaggcccacc tggaagataa gtaccgctat   9660
ctgtttaaac aggtggccag ctctaccggc ttctgcgacc agagaaggct gggactgctg   9720
ctgcacgact ccatccagat ccccagacag ctgggagagg tggcctcctt cggcggcagc   9780
aacatcgagc ctagcgtgcg gagctgcttc cagttcgcca caacaagcc cgagatcgaa   9840 gccgccctgt tcctggattg gatgaggctg gaacctcagt ctatggtctg gctgcccgtg   9900
ctgcacaggg tggccgctgc cgagacagcc aagcaccagg ccaagtgcaa catctgcaaa   9960
gagtgcccca tcatcggctt cagatatcgg tccctgaagc acttcaacta cgatatctgc  10020
cagagctgct tcttcagcgg cagagtggcc aagggccaca agatgcatta ccccatggtg  10080
gaatactgca ccccccaccac cagcggcgag gatgtgcggg acttcgccaa ggtgctgaag  10140
aacaaattca ggactaagcg ctacttcgct aagcacccta gaatgggcta tctgcctgtg  10200
```

```
cagacagtgc tggaaggcga caacatggaa accccgtga ccctgatcaa cttttggccc    10260
gtggacagcg cacctgccag cagtcctcag ctgagccacg acgacaccca cagcagaatc    10320
gagcactacg cctccagact ggccgagatg gaaaacagca acggcagcta cctgaacgac    10380
agcatctccc ccaacgagag catcgacgac gagcatctgc tgatccagca ctactgccag    10440
tccctgaacc aggacagccc cctgagccag cccagatccc ctgcccagat cctgatctcc    10500
ctggaaagcg aggaaagagg cgagctggaa aggatcctgg ctgacctgga agaggaaaac    10560
agaaacctgc aggccgagta cgacagactg aagcagcagc acgagcacaa gggcctgagc    10620
cccctgccta gcccccctga gatgatgccc accagccctc agagcccag ggacgctgag    10680 ctgatcgccg aggccaagct gctgaggcag cataagggcc ggctggaagc ccggatgcag    10740
atcctggaag atcacaacaa acagctgaa agccagctgc acagactcag acagctgctg    10800
gaacagcccc aggccgaggc taaagtgaac ggcaccacag tgtccagccc ctccacctcc    10860
ctgcagagat ccgacagcag ccagcccatg ctgctgagag tggtcggaag ccagaccagc    10920
gacagcatgg gcgaagagga tctgctgagc ccccctcagg acaccagcac aggactggaa    10980
gaagtgatgg aacagctgaa caacagcttc cccagcagca gaggcagaaa caccccggc    11040 aagcccatgc gcgaggacac catgtga                                       11067
```